(12) United States Patent
Clifford et al.

(10) Patent No.: US 7,615,013 B2
(45) Date of Patent: Nov. 10, 2009

(54) METHODS AND DEVICES FOR CUTTING AND COLLECTING SOFT TISSUE

(75) Inventors: Mark J. Clifford, Los Altos, CA (US); Scott C. Anderson, Sunnyvale, CA (US); James W. Vetter, Portola Valley, CA (US); Daniel M. Brounstein, Fremont, CA (US); Ary S. Chernomorsky, Walnut Creek, CA (US)

(73) Assignee: Rubicor Medical, Inc., Redwood City, CA (US)

( * ) Notice: Subject to any disclaimer, the term of this patent is extended or adjusted under 35 U.S.C. 154(b) by 398 days.

(21) Appl. No.: 11/441,627

(22) Filed: May 25, 2006

(65) Prior Publication Data

US 2006/0224083 A1 Oct. 5, 2006

Related U.S. Application Data

(63) Continuation of application No. 10/601,300, filed on Jun. 18, 2003, now Pat. No. 7,122,011.

(51) Int. Cl.
*A61B 10/00* (2006.01)
(52) U.S. Cl. .................... 600/564; 600/567; 606/167
(58) Field of Classification Search ......... 600/564–568; 606/113, 114, 161, 164, 167, 170
See application file for complete search history.

(56) References Cited

U.S. PATENT DOCUMENTS

| | | |
|---|---|---|
| 1,813,902 A | 7/1931 | Bovie |
| 2,816,552 A | 12/1957 | Hoffman |
| 3,320,957 A | 5/1967 | Sokolik |
| 3,732,858 A | 5/1973 | Banko |
| 3,749,085 A | 7/1973 | Willson |
| 3,910,279 A | 10/1975 | Okada et al. |
| 3,955,578 A | 5/1976 | Chamness et al. |
| 4,099,518 A | 7/1978 | Baylis et al. |
| 4,245,653 A | 1/1981 | Weaver |
| 4,347,846 A | 9/1982 | Dormia |

(Continued)

FOREIGN PATENT DOCUMENTS

DE 195 28 440 A1 2/1997

(Continued)

OTHER PUBLICATIONS

International Search Report mailed Apr. 13, 2005, in corresponding International Application No. PCT/US04/19493, filed Jun. 17, 2004 (3pgs).

(Continued)

*Primary Examiner*—Max Hindenburg
*Assistant Examiner*—Jonathan M Foreman
(74) *Attorney, Agent, or Firm*—Young Law Firm, P.C.

(57) ABSTRACT

Devices and methods for collecting or cutting and collecting a specimen from a mass of tissue within a patient. The device may include a specimen collection assembly including a flexible membrane that isolates collected specimen from the surrounding tissue. The collection device may also include structures that draw the collected specimen toward the shaft and/or otherwise ease the insertion and retraction of the device and the collected specimen from the patient through a small incision.

13 Claims, 17 Drawing Sheets

U.S. PATENT DOCUMENTS

| | | |
|---|---|---|
| 4,611,594 A | 9/1986 | Grayhack |
| 4,650,466 A | 3/1987 | Luther |
| 4,890,611 A | 1/1990 | Monfort |
| 4,903,696 A | 2/1990 | Stasz et al. |
| 4,966,604 A | 10/1990 | Reiss |
| 5,071,424 A | 12/1991 | Reger |
| 5,083,570 A | 1/1992 | Mosby |
| 5,100,423 A | 3/1992 | Fearnot |
| 5,147,355 A | 9/1992 | Friedman et al. |
| 5,152,293 A | 10/1992 | Vonesh et al. |
| 5,156,610 A | 10/1992 | Reger |
| 5,174,296 A | 12/1992 | Watanabe et al. |
| 5,176,688 A | 1/1993 | Narayan |
| 5,192,291 A | 3/1993 | Pannek |
| 5,211,651 A | 5/1993 | Reger |
| 5,217,479 A | 6/1993 | Shuler |
| 5,224,488 A | 7/1993 | Neuffer |
| 5,224,945 A | 7/1993 | Pannek et al. |
| 5,282,484 A | 2/1994 | Reger |
| 5,308,321 A | 5/1994 | Castro |
| 5,318,576 A | 6/1994 | Plassche |
| 5,325,860 A | 7/1994 | Seward et al. |
| 5,415,656 A | 5/1995 | Tihon et al. |
| 5,441,510 A | 8/1995 | Simpson et al. |
| 5,527,326 A | 6/1996 | Hermann |
| 5,554,163 A | 9/1996 | Shturman |
| 5,630,426 A | 5/1997 | Eggers et al. |
| 5,632,754 A | 5/1997 | Farley et al. |
| 5,672,172 A | 9/1997 | Zupkas |
| 5,709,697 A | 1/1998 | Ratcliff |
| 5,766,191 A | 6/1998 | Trerotola |
| 5,794,626 A | 8/1998 | Kieturakis |
| 5,795,308 A | 8/1998 | Russin |
| 5,895,399 A | 4/1999 | Barbut et al. |
| 5,913,855 A | 6/1999 | Gough et al. |
| 5,928,159 A | 7/1999 | Eggers et al. |
| 5,928,164 A | 7/1999 | Burbank |
| 5,947,964 A | 9/1999 | Eggers et al. |
| 5,954,655 A | 9/1999 | Hussman |
| 5,954,670 A | 9/1999 | Baker |
| 6,015,390 A | 1/2000 | Krag |
| 6,022,362 A | 2/2000 | Lee |
| 6,036,708 A | 3/2000 | Sciver |
| 6,063,082 A | 5/2000 | DeVore |
| 6,080,149 A | 6/2000 | Huang |
| 6,080,151 A | 6/2000 | Swartz et al. |
| 6,096,053 A | 8/2000 | Bates |
| 6,099,534 A | 8/2000 | Bates |
| 6,106,524 A | 8/2000 | Eggers et al. |
| 6,179,860 B1 | 1/2001 | Fulton, III et al. |
| 6,221,006 B1 | 4/2001 | Dubrul et al. |
| 6,238,389 B1 | 5/2001 | Paddock et al. |
| 6,264,663 B1 | 7/2001 | Cano |
| 6,280,450 B1 | 8/2001 | McGuckin, Jr. |
| 6,325,797 B1 | 12/2001 | Stewart et al. |
| 6,331,166 B1 | 12/2001 | Burbank |
| 6,387,056 B1 | 5/2002 | Kieturakis |
| 6,508,773 B2 | 1/2003 | Burbank et al. |
| 6,514,248 B1 | 2/2003 | Eggers et al. |
| 6,602,204 B2 | 8/2003 | Dubrul et al. |
| 6,605,047 B2 | 8/2003 | Zarins et al. |
| 6,780,179 B2 | 8/2004 | Lee et al. |
| 2001/0047169 A1 | 11/2001 | McGuckin, Jr. |
| 2002/0058885 A1 | 5/2002 | Burbank et al. |
| 2003/0229343 A1 | 12/2003 | Albrecht et al. |

FOREIGN PATENT DOCUMENTS

| | | |
|---|---|---|
| DE | 197 06 751 A1 | 2/1997 |
| EP | 0 472 368 B1 | 2/1992 |
| EP | 0 829 232 A2 | 3/1998 |
| EP | 0 829 232 A3 | 3/1998 |
| EP | 0 908 156 B1 | 11/2003 |
| FR | 2 275 226 | 5/1975 |
| GB | 1 331 468 | 9/1973 |
| GB | 2 204 496 A | 11/1988 |
| GB | 2 311 468 A | 1/1997 |
| NL | 1.004723 | 9/1912 |
| SU | 1235497 A1 | 6/1986 |
| SU | 1355266 A1 | 11/1987 |
| WO | WO 92/20291 | 11/1992 |
| WO | WO 95/02370 | 1/1995 |
| WO | WO 95/02371 | 1/1995 |
| WO | WO 96/29946 | 10/1996 |
| WO | WO 98/08441 | 3/1998 |
| WO | WO 99/01074 | 1/1999 |
| WO | WO 99/04704 | 2/1999 |
| WO | WO 99/43262 | 9/1999 |
| WO | WO 99/44506 | 10/1999 |
| WO | WO 99/53851 | 10/1999 |
| WO | WO 00/10471 | 3/2000 |
| WO | WO 00/12009 | 3/2000 |
| WO | WO 00/16697 | 3/2000 |
| WO | WO 00/30531 | 6/2000 |
| WO | WO 00/33743 | 6/2000 |
| WO | WO 00/44295 | 8/2000 |
| WO | WO 00/45854 | 8/2000 |
| WO | WO 00/74561 A1 | 12/2000 |
| WO | WO 01/28445 A1 | 4/2001 |
| WO | WO 01/28446 A1 | 4/2001 |

OTHER PUBLICATIONS

Written Opinion mailed Apr. 13, 2005, in corresponding International Application No. PCT/US04/19493, filed Jun. 17, 2004 (3pgs).

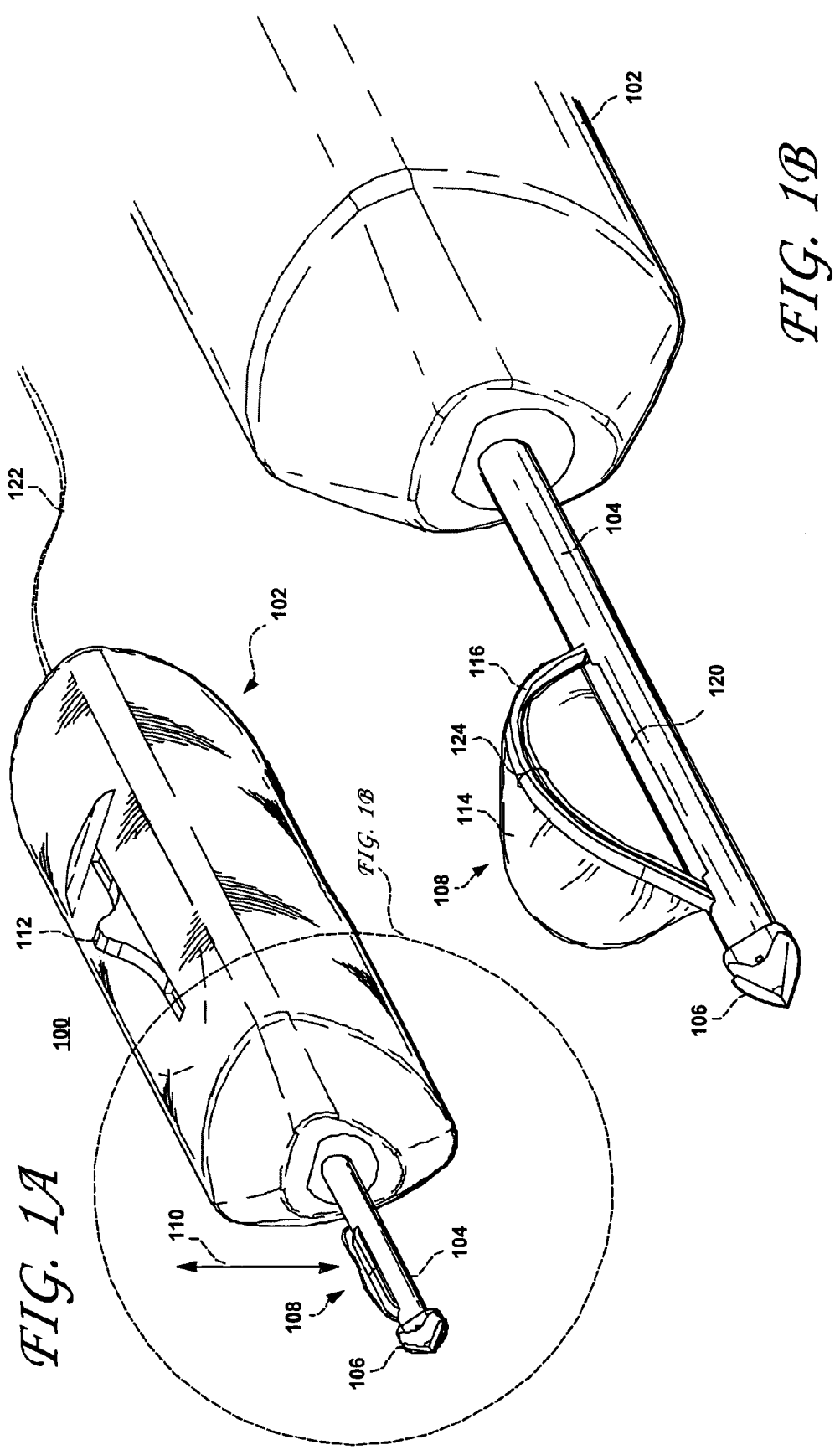

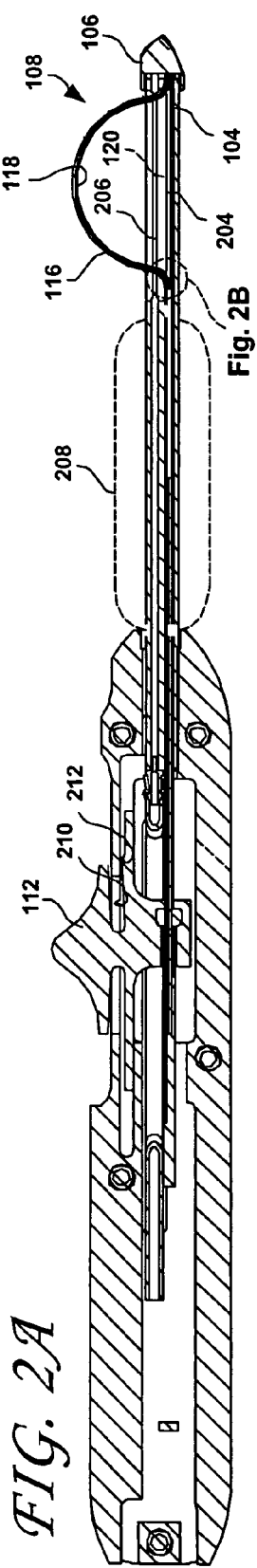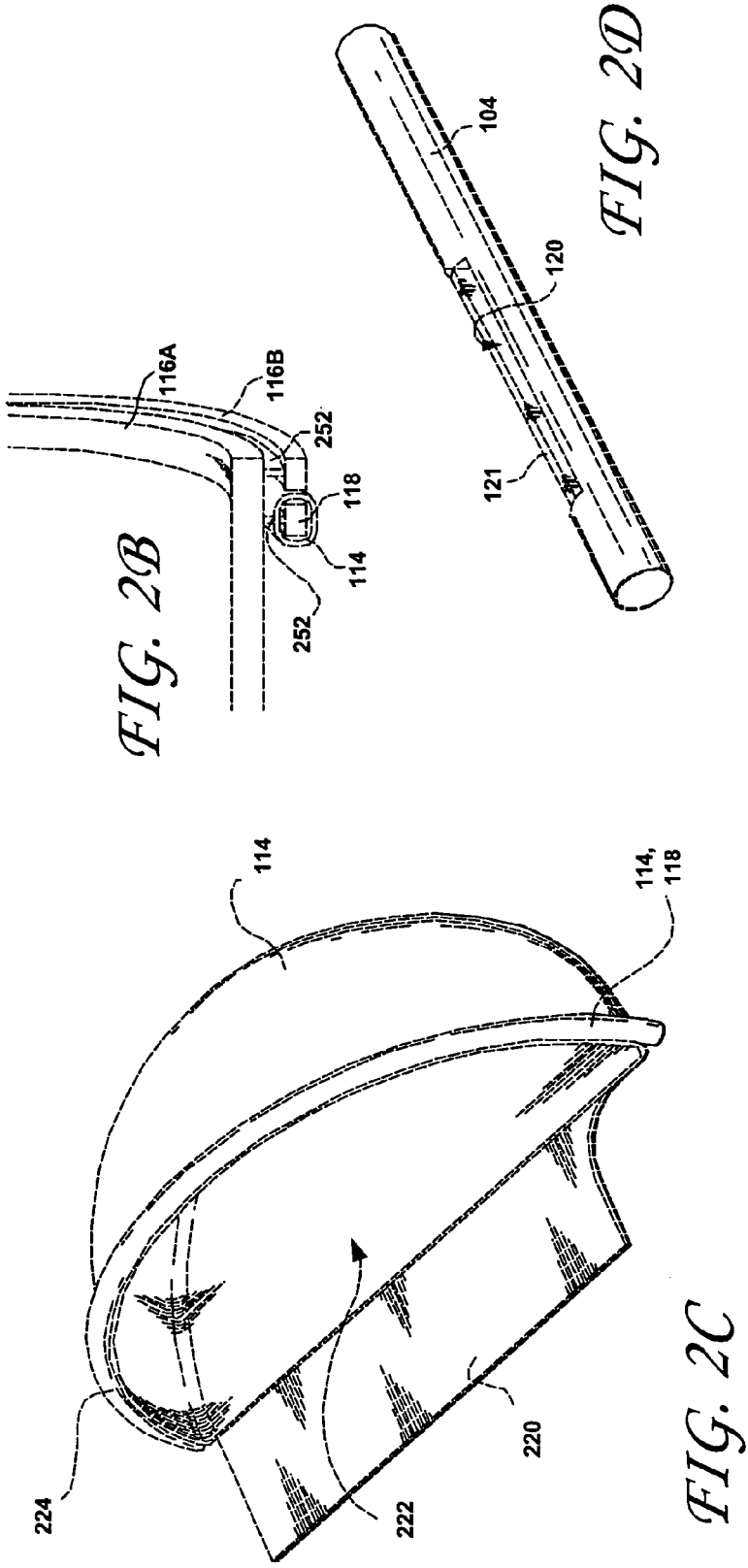

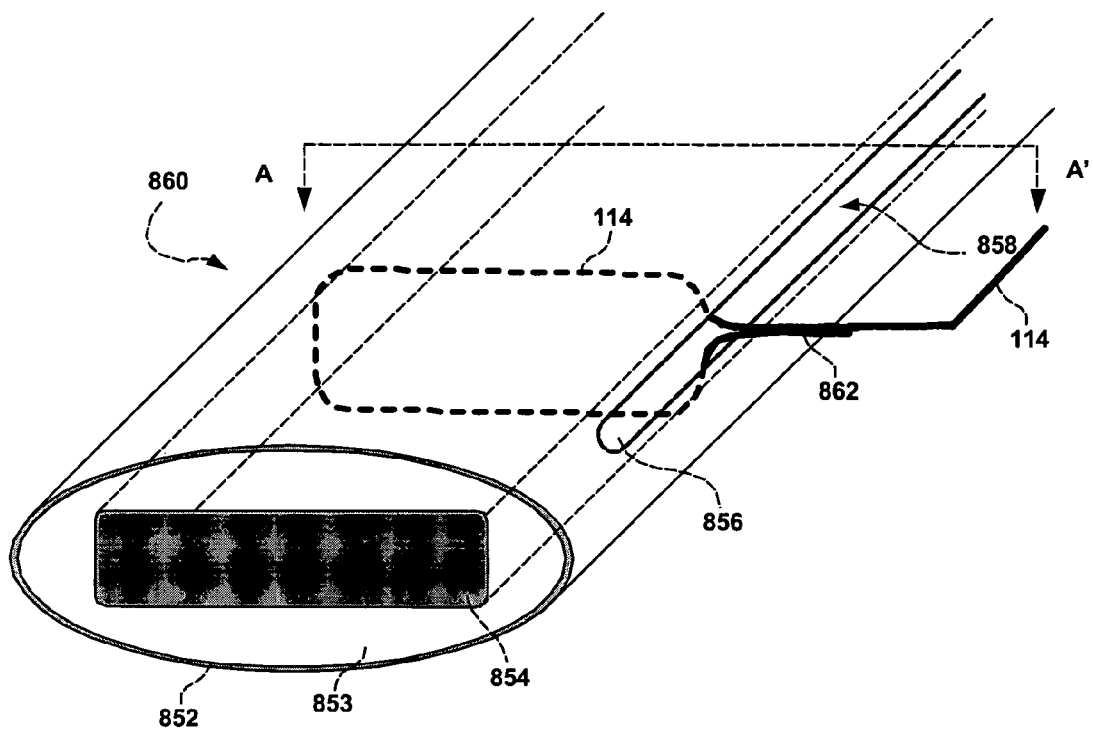
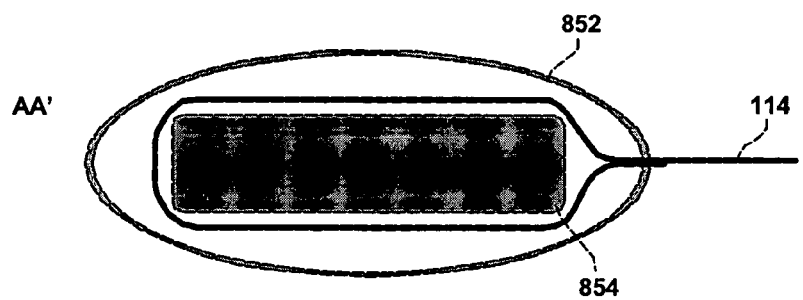
FIG. 8C

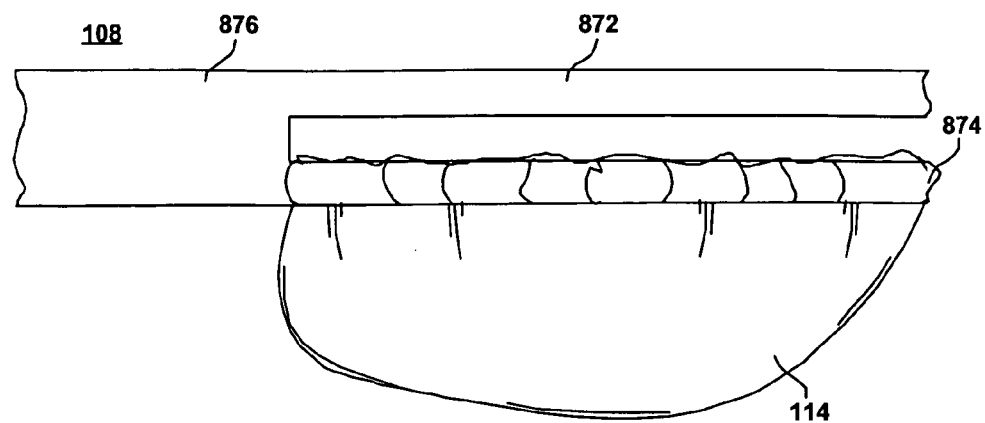
FIG. 8D
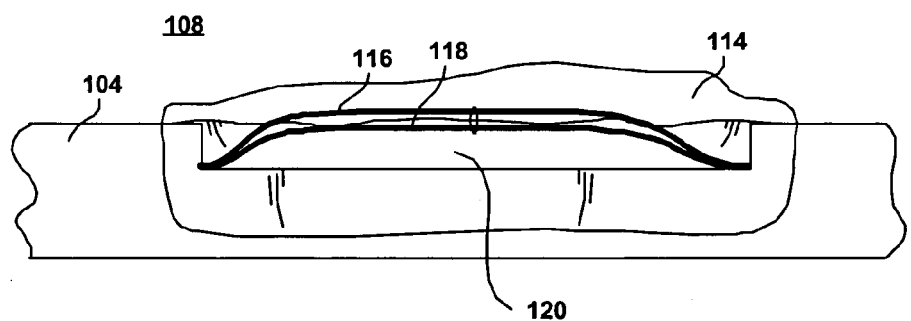
FIG. 8E
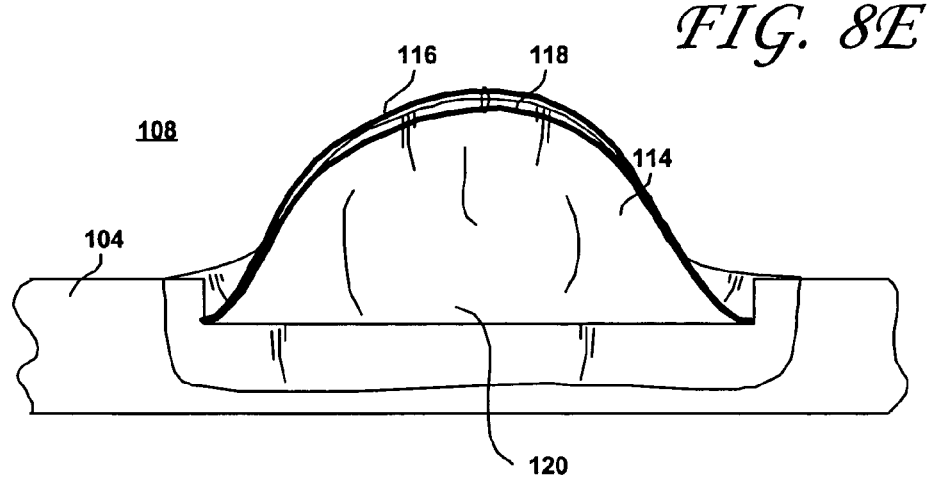

METHODS AND DEVICES FOR CUTTING AND COLLECTING SOFT TISSUE

This application is a continuation of prior application Ser. No. 10/601,300, filed Jun. 18, 2003, which application is hereby incorporated herein in its entirety and from which application priority is hereby claimed under 35 U.S.C. §120.

BACKGROUND OF THE INVENTION

1. Field of the Invention

The present invention pertains to the field of soft tissue excisional devices and methods. In particular, the present invention relates to the field of devices and methods for excising specimen from soft tissue, such as breast tissue, for example.

2. Description of the Related Art

Breast cancer is a major threat and concern to women. Early detection and treatment of suspicious or cancerous lesions in the breast has been shown to improve long-term survival of the patient. The trend is, therefore, to encourage women not only to perform monthly self-breast examination and obtain a yearly breast examination by a qualified physician, but also to undergo annual screening mammography commencing at age 40. Mammography is the only screening modality available today that can detect small, nonpalpable lesions. These nonpalpable lesions may appear as opaque densities relative to normal breast parenchyma and fat or as clusters of microcalcifications.

The conventional method for diagnosing, localizing and excising nonpalpable lesions detected by mammography generally involves a time-consuming, multi-step process. First, the patient goes to the radiology department where the radiologist finds and localizes the lesion either using mammography or ultrasound guidance. Once localized, a radio-opaque wire is inserted into the breast. The distal end of the wire may include a small hook or loop. Ideally, this is placed adjacent to the suspicious area to be biopsied. The patient is then transported to the operating room. Under general or local anesthesia, the surgeon performs a procedure called a needle-localized breast biopsy. In the needle-localized breast biopsy, the surgeon, guided by the wire previously placed in the patient's breast, excises a mass of tissue around the distal end of the wire. The specimen is sent to the radiology department where a specimen radiograph is taken to confirm that the suspicious lesion is contained within the excised specimen. Meanwhile, the surgeon, patient, anesthesiologist and operating room staff, wait in the operating room for confirmation of that fact from the radiologist before the operation is completed. The suspicious lesion should ideally be excised in toto with a small margin or rim of normal breast tissue on all sides. Obtaining good margins of normal tissue is extremely dependent upon the skill and experience of the surgeon, and often an excessively large amount of normal breast tissue is removed to ensure that the lesion is located within the specimen. This increases the risk of post-operative complications, including bleeding and permanent breast deformity. As 80% of breast biopsies today are benign, many women unnecessarily suffer from permanent scarring and deformity from such benign breast biopsies.

More recently, less invasive techniques have been developed to sample or biopsy the suspicious lesions to obtain a histological diagnosis. The simplest of the newer techniques is to attempt visualization of the lesion by external ultrasound. If seen by external ultrasound, the lesion can be biopsied while being continuously visualized. This technique allows the physician to see the biopsy needle as it actually enters the lesion, thus ensuring that the correct area is sampled. Current sampling systems for use with external ultrasound guidance include a fine needle aspirate, core needle biopsy or vacuum-assisted biopsy devices.

Another conventional technique localizes the suspicious lesion using stereotactic digital mammography. The patient is placed prone on a special table that includes a hole to allow the designated breast to dangle therethrough. The breast is compressed between two mammography plates, which stabilizes the breast to be biopsied and allows the digital mammograms to be taken. At least two images are taken at two angular positions to obtain stereotactic views. The x, y and z coordinates targeting the lesion are calculated by a computer. The physician then aligns a special mechanical stage mounted under the table that places the biopsy device into the breast to obtain the sample or samples. There are believed to be three methods available to biopsy lesions using a stereotactic table: (1) fine needle aspiration, (2) core needle biopsy and (3) vacuum-assisted core needle biopsy.

Fine needle aspiration uses a small gauge needle, usually 20 to 25 gauge, to aspirate a small sample of cells from the lesion or suspicious area. The sample is smeared onto slides that are stained and examined by a cytopathologist. In this technique, individual cells in the smears are examined, and tissue architecture or histology is generally not preserved. Fine needle aspiration is also very dependent upon the skill and experience of the operator and can result in a high non-diagnostic rate (up to about 83%), due to inadequate sample collection or preparation.

Core needle biopsy uses a larger size needle, usually 14 gauge to sample the lesion. Tissue architecture and histology are preserved with this method. A side-cutting device, consisting of an inner trough with an outer cutting cannula is attached to a spring-loaded device for a rapid semi-automated firing action. After the lesion is localized, local anesthetic is instilled and a small incision is made in the skin with a scalpel. The device enters the breast and the needle tip is guided into the breast up to the targeted lesion. The device is fired. First, the inner cannula containing the trough rapidly penetrates the lesion. Immediately following this, the outer cutting cannula rapidly advances over the inner cannula cutting a sample of tissue off in the trough. The whole device is then removed and the sample retrieved. Multiple penetrations of the core needle through the breast and into the lesion are required to obtain an adequate sampling of the lesion. Over 10 samples have been recommended by some.

The vacuum-assisted breast biopsy system is a larger semi-automated side-cutting device. It is usually 11 gauge in diameter and is more sophisticated than the core needle biopsy device. Multiple large samples can be obtained from the lesion without having to reinsert the needle each time. A vacuum is added to suck the tissue into the trough. The rapid firing action of the spring-loaded core needle device is replaced with an oscillating outer cannula that cuts the breast tissue off in the trough. The physician controls the speed at which the outer cannula advances over the trough and can rotate the alignment of the trough in a clockwise fashion to obtain multiple samples.

If a fine needle aspirate, needle core biopsy or vacuum-assisted biopsy shows malignancy or a specific benign diagnosis of atypical hyperplasia, then the patient needs to undergo another procedure, the traditional needle-localized breast biopsy, to fully excise the area with an adequate margin of normal breast tissue. Sometimes the vacuum-assisted device removes the whole targeted lesion. If this occurs, a small titanium clip should be placed in the biopsy field. This clip marks the area if a needle-localized breast biopsy is subsequently required for the previously mentioned reasons.

Another method of biopsying the suspicious lesion utilizes a large end-cutting core device measuring 0.5 cm to 2.0 cm in diameter. This also uses the stereotactic table for stabilization and localization. After the lesion coordinates are calculated and local anesthesia instilled, an incision large enough is permit entry of the bore is made at the entry site with a scalpel. The breast tissue is cored down to and past the lesion. Once the specimen is retrieved, the patient is turned onto her back and the surgeon cauterizes bleeding vessels under direct vision. The incision, measuring 0.5 to larger than 2.0 cm is sutured closed.

The stereotactic table requires awkward positioning of the patient and may be extremely uncomfortable. The woman must lie prone during the entire procedure, which may be impossible for some patients. In addition, the lesion to be biopsied must be in the center working area of the mammography plates. This may be extremely difficult and uncomfortable for the patient if the lesion is very posterior near the chest wall or high towards the axilla.

The woman is subjected to increased radiation exposure as multiple radiographs are required throughout the course of the procedure to: (1) confirm that the lesion is within the working area of the mammography plates, (2) obtain the stereotactic coordinates (at least two views), (3) verify the positioning of the biopsy needle prior to obtaining tissue, and (4) verify that the lesion was indeed sampled. If any difficulty is encountered during the procedure, additional radiographic exposures are required to verify correction of the problem.

Using the core needle biopsy or vacuum-assisted device, bleeding is controlled only by manual pressure. Bleeding is generally not an issue with fine needle aspiration, but is a legitimate complication of the former two methods. Ecchymoses, breast edema and hematomas can occur. This causes increased post-procedural pain and delays healing. Rarely, the patient may require an emergency operation to control and evacuate a tense hematoma.

Another major concern is the possibility of tumor dissemination. The core needle biopsy and vacuum-assisted devices both cut into the tumor and carve out multiple samples for examination. While cutting into the tumor, cancerous cells may be dislodged. Cutting across blood vessels at the same time may allow the freed cancerous cells access to the blood stream, thus possibly seeding the tumor beyond its original locus. The long-term consequences of tumor seeding with the risk of blood borne metastases are unknown at this time, as the techniques are relatively new. However, documented instances of cancerous cells seeding locally into needle tracks exist. There are numerous reports of metastases growing in needle tracks from previous biopsies of a cancerous mass. Most of these are from lung or liver cancers. However, at least one case of mucinous carcinoma of the breast growing in a needle track has been reported. The long-term consequences of neoplasm seeding into needle tracks are currently unknown, again because the techniques are relatively new. Some recommend excision of the entire needle track, including the skin entry site, during the definitive surgical procedure for a diagnosed cancer, whether it is a lumpectomy or a mastectomy. Others assume that with a lumpectomy, the postoperative radiation therapy will destroy any displaced cancer cells in the needle track. With the trend towards treating very small cancers only by excision and without a post-excision course of radiation therapy, the risk of cancer cells metastasizing and growing in needle tracks is very real.

The large core cutting device (0.5 cm to 2.0 cm) generally eliminates the risk of needle track seeding as it is designed to excise the lesion intact. A stereotactic table is required with the same inherent awkwardness for the patient, as discussed above. Bleeding is controlled, albeit manually, requiring that the patient wait until the end of the procedure to be turned over. Compression is used to stabilize the breast and localize the lesions. The breast, however, may be torqued and distorted between the compression plates such that when the plates are removed after the biopsy, the large core track left behind may not be straight, but actually tortuous. This can result in permanent breast deformity.

The location of the insertion site into the breast is dictated by the positioning of the breast in the machine and not by the physician. The entry site is usually away from the cosmetically preferred nipple-areolar complex and is usually located on the more exposed areas of the breast. For the fine needle aspirate, core biopsy and vacuum-assisted devices, the incision is usually very small and the scar almost unappreciable. However, in the case of the large core biopsy device (0.5 to 2.0 cm), a large incision is needed. Such a large incision often results in a non-aesthetically placed scar.

The newer conventional minimally invasive breast biopsy devices have improved in some ways the ability to diagnose mammographically detected nonpalpable lesions. These devices give the patient a choice as to how she wants the diagnosis to be made. Moreover, these devices are substantially less expensive than the older traditional needle-localized breast biopsy. They are not, however, the final solution. Due to the above-discussed problems and risks associated with compression, needle-track seeding, blood borne metastases, bleeding, radiation exposure and awkwardness of the stereotactic table, more refined devices and methods are needed to resolve these issues. Also, the conventional biopsy devices do not consider margins in their excisions and if cancer is diagnosed, the patient must undergo a needle-localized breast lumpectomy to ensure that adequate margins are removed around the cancer. Devices and methods, therefore, must address the problem of obtaining adequate margins so that a second procedure is not required. Margins, moreover, cannot be assessed while the breast is being compressed.

Commonly assigned Pat. No. 6,022,362, discloses a novel approach to soft tissue excisional devices. As disclosed therein, the excisional device includes independently actuable cutting and collection tools. As shown therein, the device may include a cutting tool attached near the distal tip of the device. At least a distal portion of the cutting tool is configured to selectively bow out of the window and to retract within the window. One embodiment of the device described in this patent also includes an independently actuable tissue collection device that is separate from the cutting device and that is also externally attached near the distal end of the device. In this configuration, the tissue collection device independently collects the tissue severed by the cutting tool as the excisional is rotated and the cutting tool is independently bowed.

Such a device may tissue cut and collect relatively large specimens. Once collected, the specimen must be removed from the mass of tissue from which it was excised and must also be removed from the patient. This presence of such a collected specimen may create non-insignificant drag on the device as the physician retracts the device from the patient. The type of tissue may also affect the ease with which the device and collected specimen may be removed from the patient. For example, fibrous tissue may make both insertion and retraction of the device more difficult than they would otherwise be the case in fatty or highly vascularized tissue. Moreover, such a device may also cut and collect specimens that are larger than the percutaneous incision (preferably 1 cm or less in length) in which the device is inserted. What are needed, therefore, are means for easing insertion and retraction of the device and its collected specimen from its environment of use.

SUMMARY OF THE INVENTION

The present invention, according to another embodiment thereof may be viewed as a device for collecting a specimen from a mass of tissue, comprising: a shaft; a specimen collection assembly configured to slide between the proximal and distal ends of the shaft and to selectively assume an expanded configuration and a retracted configuration, the specimen collection assembly including a flexible membrane configured to collect the specimen and to isolate the collected specimen from the mass of tissue.

A portion of the flexible membrane may be attached to the distal end of the shaft. The specimen collection assembly may include a cutting portion for cutting the specimen from a surrounding tissue. The flexible membrane may be configured to isolate the collected specimen from the mass of tissue. The shaft may define a proximal and a distal end and a channel between the proximal and distal ends and the specimen collection assembly may be configured to slide within the channel between the proximal and distal ends of the shaft. The shaft may define a proximal and a distal end and comprises a rail between the proximal and distal ends and the specimen collection assembly may be configured to slide on the rail between the proximal and distal ends of the shaft.

According to yet another embodiment thereof, the present invention is a method of collecting a specimen from a mass of tissue, comprising the steps of providing a tissue collection device comprising a shaft and a specimen collection assembly, the shaft defining a proximal and a distal end, the specimen collection assembly being configured to slide between the proximal and distal ends and to selectively expand away from the shaft and to contract toward the shaft, the specimen collection assembly including a flexible membrane configured to collect the specimen; inserting the tissue collection device within the mass of tissue; expanding the specimen collection assembly and collecting the specimen within the flexible membrane; retracting the specimen collection assembly with the specimen collected within the flexible membrane; sliding the retracted specimen collection assembly toward the proximal end of the shaft with the specimen collected within the flexible membrane.

The tissue collection device in the providing step may include a tissue cutting portion to cut the specimen from the mass of tissue. The collecting step may collect the specimen cut from the cutting portion. The method may also include a step of sliding the specimen collection assembly toward the distal end of the shaft before the inserting step. In the inserting step, the tissue collection device may be in a configuration in which the specimen collection assembly may be slid toward the distal end of the shaft. The method may further include a step of sliding the specimen collection assembly toward the distal end of the shaft before the expanding and collecting steps. The tissue collection device in the providing step may be configured such that a portion of the flexible membrane may be attached to the distal end of the shaft, and the sliding step draws the specimen collected within the flexible membrane toward the shaft. The method may also include a step of retracting the tissue collection device from the mass of tissue with the specimen collection assembly near the proximal end of the shaft and the specimen collected within the flexible membrane. The retracting step may isolate the specimen collected within the flexible membrane from the mass of tissue.

In the providing step, the shaft may define a channel between the proximal and distal ends of the shaft and the sliding step may slide the retracted specimen collection assembly within the channel. In the providing step, the shaft may include a rail between the proximal and distal ends of the shaft and the sliding step slides the retracted specimen collection assembly on the rail.

The present invention, according to yet another embodiment thereof, is a method of collecting a specimen from a mass of tissue, comprising the steps of providing a tissue collection device comprising a shaft defining a proximal and a distal end, a sleeve disposed over at least a portion of the shaft and a specimen collection assembly configured to selectively expand away from the shaft and to retract toward the shaft and including a flexible membrane configured to collect the specimen, at least a portion of the flexible membrane being disposed between the shaft and the sleeve; inserting the tissue collection device within the mass of tissue with the sleeve covering at least a portion of the sleeve and at least a portion of the specimen collection assembly; expanding the specimen collection assembly and collecting the specimen within the flexible membrane, the expanding specimen collection assembly pulling the flexible membrane out from between the shaft and the sleeve, and retracting the specimen collection assembly with the specimen collected within the flexible membrane.

A step may be carried out of proximally retracting the sleeve to expose the specimen collection assembly to the mass of tissue prior to the inserting step. The inserting step may be carried out with the sleeve defining a cutout aligned so as to allow the specimen collection assembly to expand and retract therethrough. The providing step may be carried out with at least the portion of the sleeve wrapped around an outer surface of the shaft.

BRIEF DESCRIPTION OF THE DRAWINGS

For a further understanding of the objects and advantages of the present invention, reference should be made to the following detailed description, taken in conjunction with the accompanying figures, in which:

FIG. 1A is perspective view of an excisional device according to an embodiment of the present invention.

FIG. 1B is a partial enlarged view of the excisional device of FIG. 1A, in which the integrated cut and collect assembly thereof is in an expanded configuration.

FIG. 2A is a cross-sectional side view of an excisional device according to an embodiment of the present invention.

FIG. 2B is a perspective view of a portion of the integrated cut and collect assembly of FIG. 2A.

FIG. 2C is a perspective view of the collection portion of the integrated cut and collect assembly, showing the manner in which the flexible membrane may be attached to the assembly and the outer surface of the shaft of the present excisional device, according to an embodiment of the present invention.

FIG. 2D is a perspective view of a shaft of the present excisional device, showing further aspects of the present invention.

FIG. 8C shows a perspective and a cross sectional view of still another exemplary configuration of the integrated cut and collect assembly of the present invention.

FIG. 8D shows yet another exemplary configuration of the integrated cut and collect assembly of the present invention, detailing the manner in which the collecting portion may be attached to the cutting portion of the integrated cut and collect assembly.

FIG. 8E shows a still further exemplary configuration of the integrated cut and collect assembly of the present invention.

DESCRIPTION OF THE INVENTION

Figure 3:
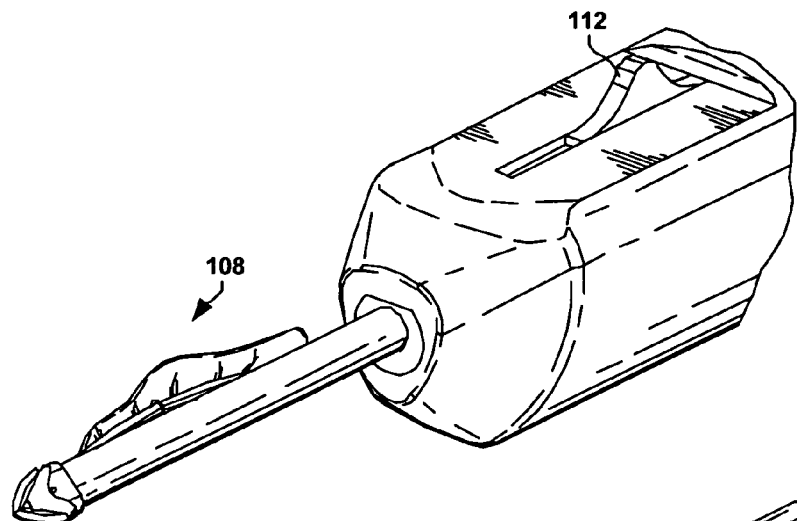
FIG. 3 is a perspective view of an excisional device according to an embodiment of the present invention, with the integrated cut and collect assembly in the retracted position.

FIG. 1A is a perspective view of an excisional device according to an embodiment of the present invention. As shown, the excisional device 100 includes a proximal section 102 that may be configured to fit the physician's hand. Extending from the proximal section 102 is a shaft 104 that may be terminated by a distal tip 106. However, an introducer may be used for the initial incision, whereupon the tip 106 may be omitted from the device 100. The distal tip 106 is configured so as to easily penetrate a mass of tissue, and may feature curvilinear cutting surfaces (best seen in FIG. 1B). The distal tip 106 may be configured to be energized by a radio frequency (RF) energy source, supplied via the electrical cord 122. However, the distal tip 106 need not be energized, as the sharpness of the cutting surfaces of the distal tip 106 is generally sufficient to easily penetrate the tissue to the target excision site. The distal tip 106 may be configured to be retractable and extendable, so as to reduce trauma, as disclosed in commonly assigned U.S. Pat. No. 7,029,451, which patent is hereby incorporated herein in its entirety. An integrated cut and collect assembly 108 is mounted near the distal tip 106 or near the distal most portion of the shaft 104. According to the present invention, the integrated cutting and collection assembly 108 is configured to cut a tissue specimen (a piece of tissue or a lesion) from the mass of tissue (e.g., breast tissue), to collect the cut specimen and to isolate the cut specimen from the surrounding tissue by, for example, encapsulating the same within a flexible bag-shaped membrane. Although the present invention finds advantageous utility in terms of excisional procedures on the female breast, it is understood that the present invention is not limited thereto. Indeed, the present methods and devices may be advantageously employed and deployed within most any mass of soft tissue. Moreover, although the present excisional device described and shown herein is presented as a hand held excisional device, it is to be understood that the proximal section 102 may be suitably modified to fit within a stereotactic unit for automated, semi-automated or manual operation.

According to the present invention, the integrated cut and collect assembly 108 includes a cutting portion and a collection portion that includes a flexible membrane 114. The collection portion of integrated cut and collect assembly 108 is attached to the cutting portion. As shown most clearly in FIG. 1B, the collection portion may be attached to the cutting portion, according to an embodiment of the present invention, by a small ring member 124 encircling both the cutting portion and part of the collecting portion so as to insure that the cutting and collection portions of the integrated cut and collect assembly 108 move together. As noted above, the cutting portion is configured to cut the specimen from the mass of tissue and the collection portion is configured to collect the cut specimen and to isolate the cut specimen from surrounding tissue. This isolation from surrounding tissue, according to the present invention, is carried out by a flexible membrane 114 that forms a part of the collecting portion of the integrated cut and collect assembly 108, as described in detail below.

The integrated cut and collect assembly 108 may be mechanically coupled to an actuator 112 such that operation of the actuator 112 causes a deployment of the integrated cut and collect assembly 108 from the retracted position shown in FIG. 1A in which the integrated cut and collect assembly 108 is at least partially retracted within a trough 120 defined within the shaft 104 to a selectable expanded position away from the shaft 104, as shown in FIG. 1B. For example, by pushing the actuator 112 in the distal direction (i.e., toward the distal tip 106), the integrated cut and collect assembly 108 transitions from the retracted position shown in FIG. 1A to a selectable variable expanded position illustrated in FIG. 1B in which the integrated cut and collect assembly 108 bows out radially relative to the longitudinal axis of the shaft 104 (i.e., in the direction of arrow 110 in FIG. 1A). The degree of bowing (expansion) of the integrated cut and collect assembly 108 depends upon the travel imposed upon the actuator 112 by the physician. In this manner, the physician may match the degree of expansion of the integrated cut and collect assembly 108 to the size of the targeted lesion or the size of the desired specimen within the mass of tissue. The degree of expansion may be varied at will during the excisional procedure by means of direct observation by means of ultrasound or some other imaging or guidance modality disposed within the shaft 104 or external to the device 100.

The cutting portion may include a ribbon 116 that is pushed out of the trough 120 to assume the bowed shape of FIG. 1B. The ribbon may be energized by an RF energy source so as to efficiently cut the specimen from the mass of tissue. A standard, off the shelf and widely available RF generator, such as a ValleyLab Force FX Generator from ValleyLab of Boulder, Colo. may advantageously be used to energize the cutting portion of the integrated cut and collect assembly 108 of the present invention, although other RF generators may also be employed to energize the cutting portion of the integrated cut and collect assembly 108 and/or the tip 106 described herein. As the excisional device is rotated during the cutting of the specimen, the ribbon 116 of the cutting portion preferably forms the leading edge of the integrated cut and collect assembly 108. The collecting portion of the integrated cut and collect assembly 108 may also include a ribbon that is mechanically coupled to the cutting portion thereof. The ribbon of the collecting portion may at least partially overlap the ribbon 116 of the cutting portion. Attached to the collecting ribbon and/or to the ribbon 116 of the cutting portion is a flexible membrane 114, which serves to collect and to isolate the collected specimen by drawing over the cut specimen and encapsulating same. The flexible membrane 114 may be shaped as a bag (a container that is closed on all sides except a selectively openable and closable opening) whose opening may be attached to both the shaft 104 and to the collecting ribbon and/or the ribbon 116 of the cutting portion of the integrated cut and collect assembly 108. Although the embodiment of the present invention shown in FIGS. 1A and 1B includes a cutting ribbon 116 and a collecting ribbon, both ribbons are expanded and retracted substantially simultaneously as they are mechanically coupled to one another to form the integrated cut and collect assembly 108, a single mechanical expandable and retractable loop. Alternatively, only a single ribbon may be present and the flexible membrane attached directly to such single ribbon, as detailed herein below. By virtue of this configuration, when the integrated cut and collect assembly 108 is in the expanded position (FIG. 1B), the bag is in an open configuration in which the tissue cut by the cutting portion is received and collected in the bag formed by the flexible membrane 114 as the device is rotated. However, when the integrated cut and collect assembly 108 is in the retracted position (FIG. 1A), the opening of the bag formed by the flexible membrane 114 is pinched shut or substantially shut, thereby trapping and encapsulating the collected specimen therein and isolating (or substantially isolating) the collected specimen from the surrounding tissue.

FIG. 2A is a cross-sectional side view of an excisional device according to an embodiment of the present invention. As shown, the actuator 112 may be mechanically coupled to the integrated cut and collect assembly 108 so that when the actuator is pushed in the proximal direction, the integrated cut and collect assembly 108 retracts within the trough 120 defined within the shaft 104. Conversely, when the actuator 112 is pushed in the distal direction, the integrated cut and collect assembly 108 is pushed out of the trough 120 and expands out of the trough 120 to assume the bowed shape shown in FIG. 2A. The ribbon or ribbons of the integrated cut and collect assembly 108 may extend back to the actuator 112 through a first lumen 204 defined within the shaft 104 and may be attached to the actuator 112 to thereby enable movement of the actuator 112 to expand and retract the integrated cut and collect assembly 108. Alternatively, the ribbon 118 of the collecting portion of the integrated cut and collect assembly 108 may only extend a fraction of the length of the cutting ribbon 116. However, as the two ribbons are mechanically coupled to one another, expansion of the cutting ribbon 116 causes the simultaneous expansion of the collecting ribbon 118 without the collecting ribbon 118 being directly attached to the actuator 112.

A second lumen 206 may also be defined within the shaft 104. The second lumen 206 may be used, for example, to evacuate smoke and/or bodily fluids from the excision site within the mass of tissue. Alternatively the second lumen 206 defined within the shaft 104 may be used to deliver a pharmaceutical agent to the excisional site, such as, for example, an anesthetic, an analgesic and/or some other agent. Other uses may be found for such lumen. An inflatable balloon 208 may be coupled to the shaft 104. The balloon 208 may be inflated with, for example, a gas (air, an inert gas or carbon dioxide, for example) or a fluid such as saline. The balloon may serve several functions. For example, the balloon 208 may be configured to massage the mass of tissue by pulsating the inflation of the balloon, may be configured as a cooling sleeve, may be configured as a tissue expander, may be configured to stabilize the device when inserted in tissue, may be configured to seal the incision through which the device is inserted, to provide hemostatis, and/or to reduce capacitive coupling to reduce tissue heating. The balloon 208 may be inflated from a lumen defined within the excisional device and supplied to the device via a suitable port defined in the proximal end of the device. The actuator 112 may define one or more protrusions 212 and an interior surface of the device may include corresponding crenellations that are collectively and cooperatively configured to provide a number of set stops to the actuator 112 along its travel path and optionally a tactile feedback for the physician, who can set the integrated cut and collect assembly 108 to predetermined degrees of expansion without looking at the device during the excisional procedure. Indeed, during the procedure, as the physician expands the integrated cut and collect assembly 108, he or she will feel periodic increases in resistance followed by a tactile and/or audible release as the protrusions 212 slip into the crenellations 210.

FIG. 2B is a perspective view of a detail of the integrated cut and collect assembly 108 of FIG. 2A. According to this embodiment, the cutting ribbon includes a first cutter ribbon 116A and a second cutter ribbon 116B that may be welded (or otherwise attached) to the first cutter ribbon 116A, as shown by weld 252. Together, the first cutter ribbon 116A and the second cutter ribbon 116B constitute the leading (and cutting) edge of the integrated cut and collect assembly 108. Behind this leading edge is the collecting portion of the integrated cut and collect assembly 108. Specifically, behind the leading edge of the cutting portion is disposed the ribbon 118 to which the flexible membrane 114 is attached. The ribbon 118 to which the flexible membrane 114 is attached may also be welded (or otherwise attached) to the first cutter ribbon 116A, as also shown at 252. The first ribbon 116A may be relatively wider than the second ribbon 116B, so as to completely overlap both the second ribbon 116B and the ribbon 118 to which the flexible membrane 114 is attached. This gives the integrated cut and collect assembly 108 necessary rigidity, while allowing the second ribbon 116B and the ribbon 118 to be reduced in size, thereby reducing space and bulk. The three ribbons 116A, 116B and 118 are preferably kept at a voltage equipotential, so as to decrease the possibility of arcing when RF power is applied to the integrated cut and collect assembly 108. According to an advantageous embodiment of the present invention, only the first ribbon 116A need be coupled to the actuator 112. As the second ribbon 116B and the ribbon 118 are mechanically coupled to the first ribbon 116A, they will move in unison with the first ribbon 116A as the actuator 112 is moved by the physician or the stereotactic unit to which the device 100 may be coupled.

FIG. 2C is a perspective view of the collection portion of the integrated cut and collect assembly, showing the manner in which the flexible membrane 114 may be attached within the assembly 108 and to the outer surface of the shaft 104 of the present excisional device 100, according to an embodiment of the present invention. As shown therein, the flexible membrane 114 may include a lumen forming portion 224 through which the ribbon 118 (see FIG. 2B) is inserted, to provide rigidity to the mouth or opening 222 of the collecting portion of the integrated cut and collect assembly 108. The ribbon 118 is attached to the cutting ribbon 116 (116A, 116B) so as to expand and retract therewith under the action of the actuator 112. The flexible membrane 114 also includes a shaft attachment tab 220, which is configured to attach the flexible membrane 114 to the shaft 104 of the present excisional device. For example, the shaft attachment tab 220 may be attached to the shaft 104 through a mechanically and biologically appropriate adhesive. The remainder of the flexible membrane 114 may be shaped as a bag, the opening or mouth 222 thereof being delimited by the shaft attachment tab 220 and the lumen forming portion 225 through which the ribbon 118 runs. Therefore, when the actuator 112 causes the integrated cut and collect assembly 108 to expand, the opening 222 of the integrated cut and collect assembly 108 is opened and when the actuator 112 causes the integrated cut and collect assembly 108 to retract at least partially within the shaft 104, the mouth 222 of the bag formed by the flexible membrane 114 closes, effectively encapsulating and isolating whatever tissue, specimen or lesion has been cut and collected therein. The tissue is isolated, as the lumen forming portion 224, when the integrated cut and collect assembly 108 is in the retracted state, may be pressed against the shaft 104, thereby interposing a layer of the flexible membrane 114 between the collected tissue and the surrounding tissue.

As an alternative, the flexible membrane 114 may be attached to an exterior surface of the device 100 and to a tube defining a lumen running at least a portion of the length of the second ribbon 118. The flexible membrane may be attached thereto by means of an adhesive, for example. Other means and structures for attaching the flexible membrane 114 to the cutting portion of the integrated cut and collect assembly 108 are disclosed herein below.

FIG. 2D is a perspective view of a shaft 104 of the present excisional device, showing further aspects thereof. As shown therein, the shaft 104 defines a trough 120 near the distal end thereof. Preferably, the trough 120 includes a ledge portion 121 that is cut out of the shaft 104. The ledge 121 allows additional room to accommodate the membrane 114 when the integrated cut and collect assembly 108 retracts within the trough 120. The ledge 121 within the trough 120 enables the integrated cut and collect assembly 108 to more fully retract within the trough 120 than would otherwise be possible without the ledge 121 by providing additional space for the membrane 114. Without the ledge 121, the bulk of the membrane 114 could hamper the full retraction of the integrated cut and collect assembly 108 into the trough 120. The integrated cut and collect assembly 108 is preferably at least partially retracted within the trough 120 when the cutting portion thereof is first energized, prior to initiating cutting of tissue. This separates the tissue to be cut from the cutting portion of the integrated cut and collect assembly 108 until the assembly has been sufficiently energized to efficiently cut through the tissue. The trough 120 is also instrumental is allowing the present excisional device to utilize a standard RF generator (e.g., one that does not rely upon feedback from an impedance sensor or the like to vary the applied power), such as the ValleyLab Force FX Generator discussed above. Keeping the integrated cut and collect assembly 108 at least partially retracted within the trough 120 also prevents excessive thermally-induced tissue damage, as all or most of the surface area of the cutting portion of the integrated cut and collect assembly 108 is kept away from the tissue until the cutting portion is fully energized (i.e., until the current density at the cutting portion of the integrated cut and collect assembly 108 is sufficient to initiate and maintain arcing). Other means and structures that find utility in enabling the RF cutting portion of the integrated cut and collect assembly 108 are disclosed in commonly assigned application Ser. No. 10/349,659, filed Jan. 23, 2003, which application is hereby incorporated herein in its entirety.

Figure 4:
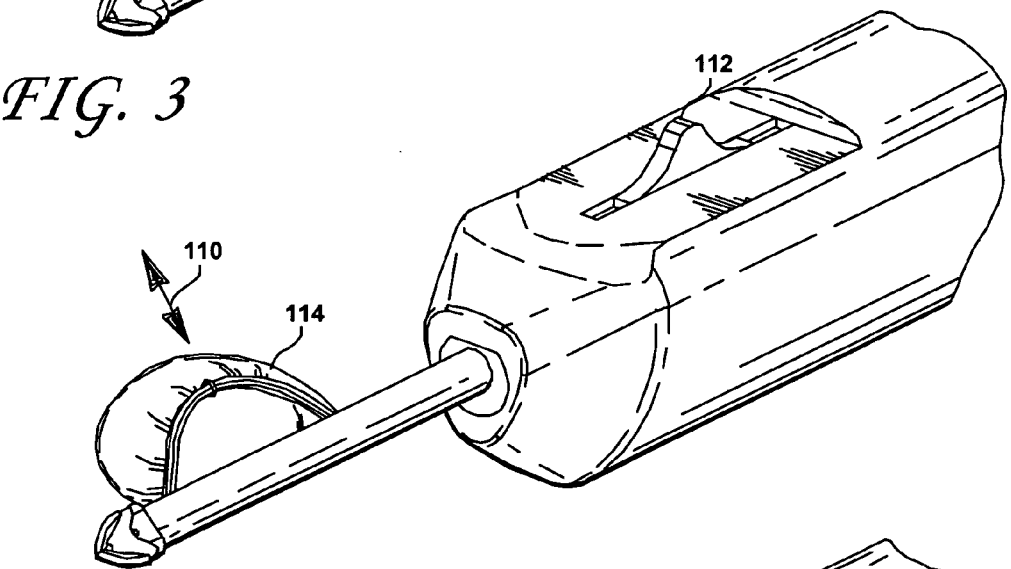
FIG. 4 shows the excisional device of FIG. 3, with the integrated cut and collect assembly in an expanded position.
Figure 5:
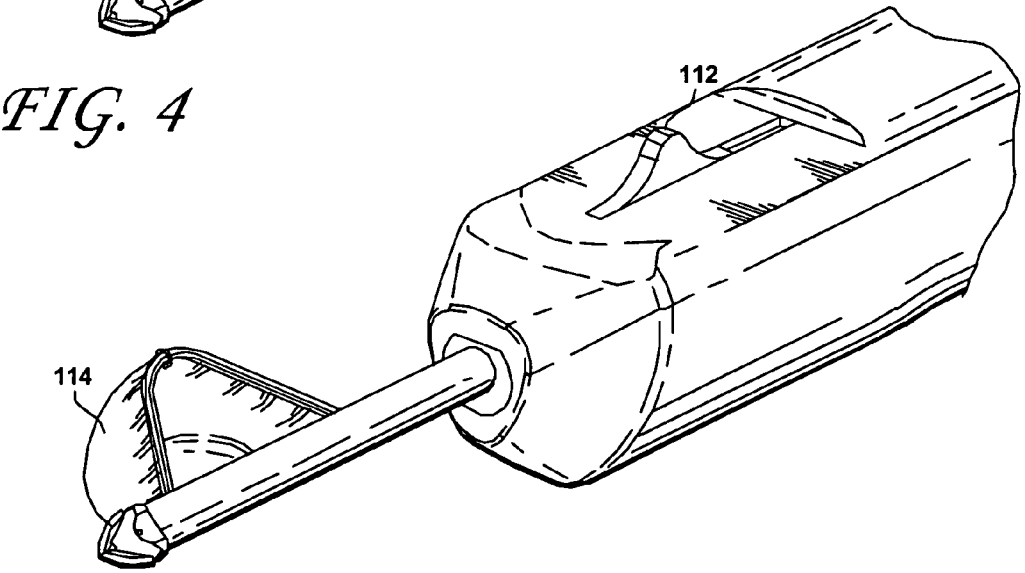
FIG. 5 shows the excisional device of FIG. 3, with the integrated cut and collect assembly in a fully expanded position.

FIGS. 3-5 collectively show the operation of integrated cut and collect assembly of the present excisional device. As shown in FIG. 3, the actuator 112 is in its proximal most position and the integrated cut and collect assembly 108 mechanically coupled thereto is in the substantially retracted position wherein both the cutting and collecting portions thereof are at least partially retracted within through 120 defined within the shaft 104. The flexible membrane 114 of the collecting portion may initially be folded, (at least partially) stowed in the trough 120 defined within the shaft 104, or simply loose. As the membrane 114 is preferably thin, smooth and flexible, it does not significantly hamper the insertion of the instrument as it penetrates the tissue mass. As shown in FIG. 4, sliding the actuator 112 in the proximal direction causes the integrated cut and collect assembly 108 to expand in the direction shown by arrow 110. This expansion causes the cutting portion of the assembly 108 to bow radially out from the shaft 104 and the deployment of the flexible membrane 114 of the collecting portion. As the flexible membrane 114 is attached both to the outer surface of the shaft 104 and to the integrated cut and collect assembly 108, expansion of the integrated cut and collect assembly 108 opens the mouth of the bag shaped flexible membrane 114 and retraction thereof (FIG. 3) closes the mouth thereof. FIG. 4 shows the device 100 in a configuration wherein the actuator 112 is engaged to its distal most position and the integrated cut and collect assembly 108 is fully expanded. By varying the position of the actuator 112, the physician may achieve a fined grained control over the deployment of the integrated cut and collect assembly 108 to suit even an irregularly-shaped and sized specimen or lesion to be cut, collected, isolated and retrieved.

The integrated cut and collect assembly 108, according to the present invention, may include one or more mechanically coupled ribbons or wires. For example, the device 100 may include a first ribbon 116 of the cutting portion and a second ribbon 118 to which the flexible membrane 114 is attached. Alternatively, the flexible membrane 114 may be attached to a trailing edge of the ribbon 116 of the cutting portion of the integrated cut and collect assembly 108. In such an embodiment, the integrated cut and collect assembly 108 does not include separate but mechanically coupled cutting and collecting portions, but instead includes only a single ribbon 116 or other (RF) cutting element to which the flexible membrane 114 is attached. Other methods and means of attaching the flexible membrane to the cutting portion are disclosed hereunder. Such methods and means may draw upon the physical mechanical structure of the cutting portion, the collecting portion, the ribbon 116 and/or 118 and the material of the flexible membrane 114.

Figure 6:
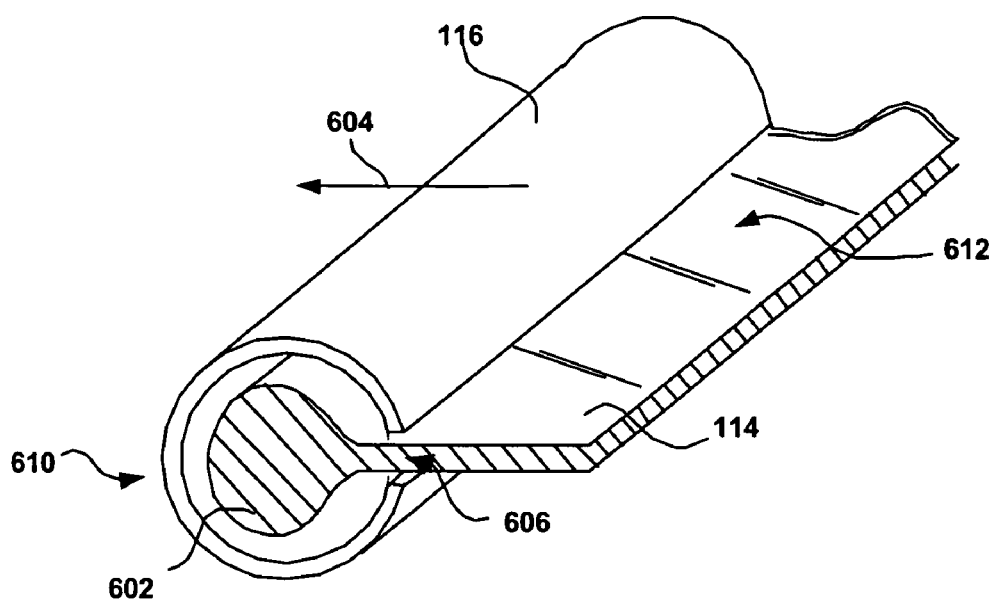
FIG. 6 shows an exemplary configuration of the integrated cut and collect assembly of the present invention, detailing the manner in which the collecting portion may be attached to the cutting portion of the integrated cut and collect assembly.

FIG. 6 shows an exemplary configuration of the integrated cut and collect assembly of the present invention, detailing one possible manner in which the collecting portion may be attached to the cutting portion of the integrated cut and collect assembly 108. As shown therein, the integrated cut and collect assembly 108 may include only a single ribbon 116. This single ribbon 116 forms the cutting portion of the assembly 108. According to this embodiment, the ribbon 116 may be configured as a flexible tube with a longitudinal slit 606 through which the flexible membrane 114 emerges. The flexible membrane 114, according to this embodiment, may include a locally thicker (bulbous, for example) portion 602 that is disposed within the interior lumen 608 defined by the tube-shaped ribbon 116. The slit 606 is oriented such that the flexible membrane 114 extends out of the trailing edge 612 of the ribbon 116. As the ribbon 116 is expanded and energized and the excisional device 100 rotated, the leading edge 610 of the ribbon 116 cuts through the tissue, while the flexible membrane 114 is deployed and trails behind, collecting, isolating and encapsulating the cut tissue. The ribbon 116 need not be shaped as a tube, but may assume any shape that efficiently cuts through the tissue and secures the flexible membrane 114 thereto. Moreover, the ribbon need not completely encircle the locally thicker portion 602 of the flexible membrane 114. The ribbon 116 may be advantageously formed of a conductive and resilient material such as stainless steel, titanium, tungsten or a shape memory metal, such as a nickel titanium alloy sold under the name of Nitinol®, for example.

Figure 7:
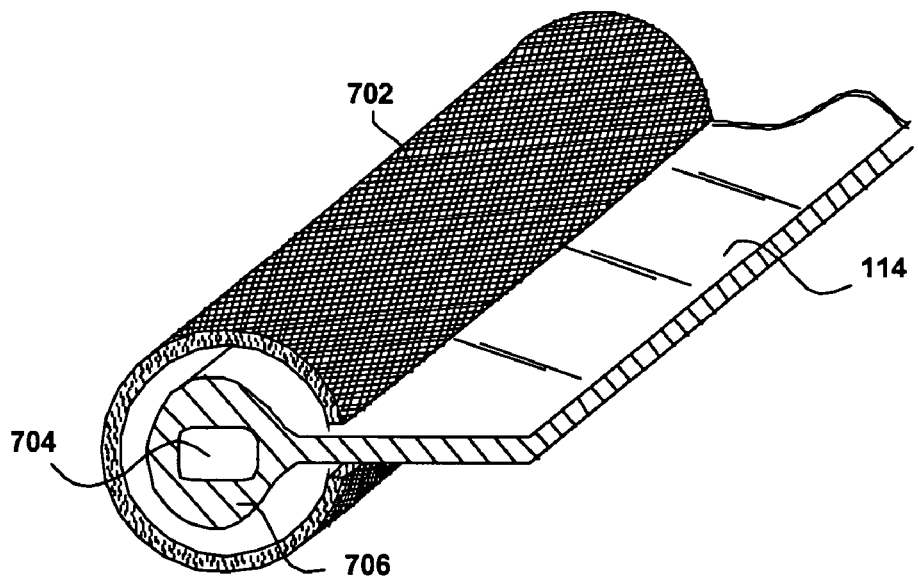
FIG. 7 shows another exemplary configuration of the integrated cut and collect assembly of the present invention.

As an alternative to the solid ribbon 116, the cutting portion of the integrated cut and collect assembly 108 may include or be formed of a plurality of wires or ribbons braided in such a manner as to form the tissue cutting ribbon, as shown at 702 in FIG. 7. To provide additional rigidity, a central reinforcing ribbon or mandrel 704 may be disposed within the interior lumen formed by the braided ribbon 702. As shown in FIG. 7, the locally thicker portion 706 of the flexible membrane 114 may be formed around the central reinforcing ribbon 704.

Figure 8A:
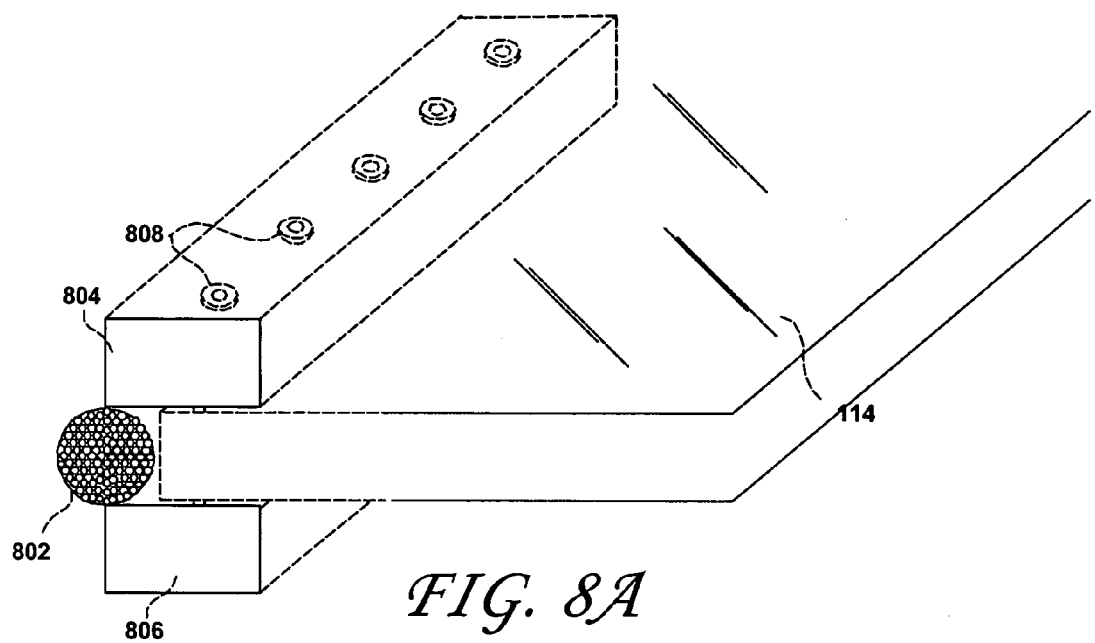
FIG. 8A shows yet another exemplary configuration of the integrated cut and collect assembly of the present invention, detailing the manner in which the collecting portion may be attached to the cutting portion of the integrated cut and collect assembly.

FIG. 8A shows another embodiment of the integrated cut and collect assembly 108. As shown, the flexible membrane 114 of the collecting portion may be sandwiched between two flexible plates 806, 808. Rivets, pins and/or welds 808 secure the two plates 804, 806 to one another with the flexible membrane 114 therebetween. The plates 804, 806 are preferably sufficiently flexible to selectively assume the retracted shape and the expanded and bowed shape of the integrated cut and collect assembly 108, as shown in FIGS. 3 and 5, respectively. The assembly of FIG. 8A may also include a solid or braided conductive (shown) ribbon or wire 802. The ribbon 802 may also be sandwiched between the two plates 804, 806 and held securely in place. In this case, the ribbon 802 defines the leading edge of the integrated cut and collect assembly 108 and the flexible membrane 114 the trailing edge thereof. The plates 804, 806 and the rivets, welds or pins 808 may be formed of a conductive material. In that case, when the ribbon 802 is energized with RF energy, the ribbon 802 and the plates 804, 806 are at a same voltage potential, which prevents or decreases the probability of arcing between the plates 804, 806 and the ribbon 802. Alternatively, only the wire or ribbon 802 may be formed of a conductive material and the plates 804, 806 and the rivets, welds or pins formed of an insulating material. In this case, only then wire or ribbon 802 is energized and cuts through the tissue.

Figure 8B:
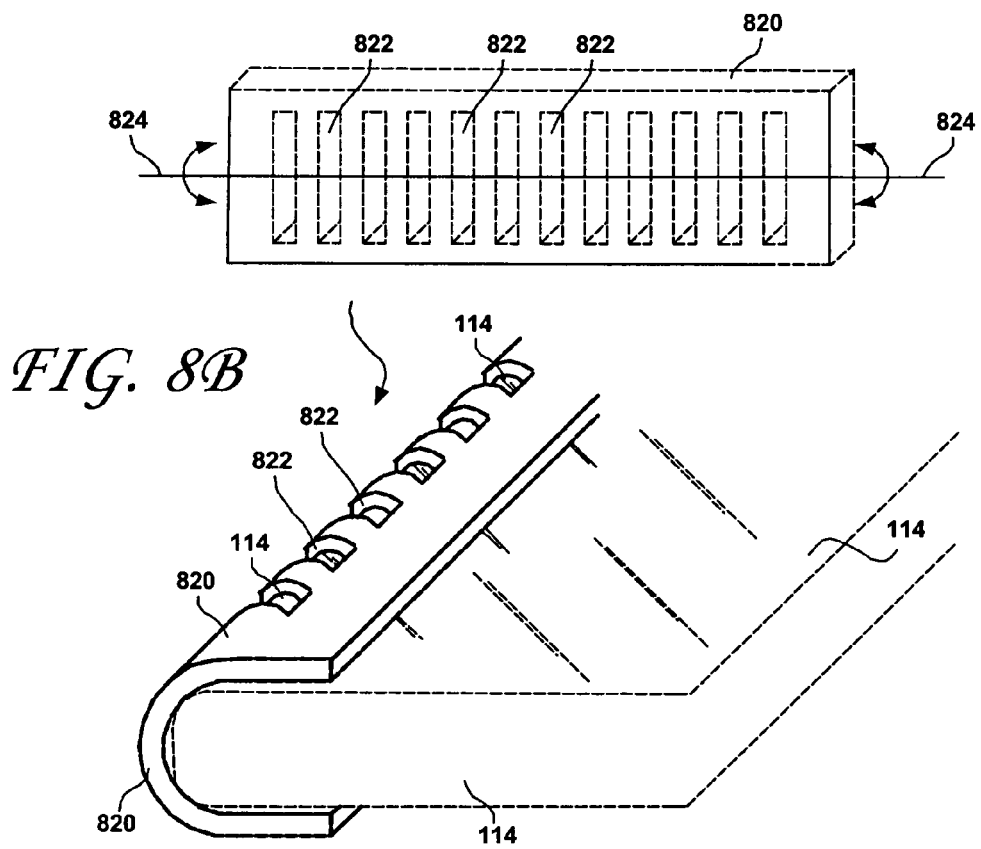
FIG. 8B shows still another exemplary configuration of the integrated cut and collect assembly of the present invention, detailing the manner in which the collecting portion may be attached to the cutting portion of the integrated cut and collect assembly.

FIG. 8B shows yet another embodiment of the integrated cut and collect assembly 108, in which the collecting portion is directly attached to the cutting portion thereof. As shown therein, the cutting portion of the integrated cut and collect assembly 108 may include a windowed conductive plate 802. This conductive (metal, for example) plate 820 is preferably a thin plate in which openings 822 are defined. The thin plate 820, according to this embodiment, forms the cutting portion of the integrated cut and collect assembly 108. This cutting portion may be formed by bending the plate 820 along the longitudinal axis 824 to secure the flexible membrane 114 between the free edges thereof. The leading edge of the integrated cut and collect assembly 108, therefore, may be formed by the bent plate 820 whereas the trailing edge thereof includes the flexible membrane 114. The openings 822 in the plate 820 may facilitate the bending thereof, so as to allow the flexible membrane 114 to be securely attached thereto. Crimping of the free edges of the plate 820 and/or an adhesive may be used to secure the flexible membrane 114 to the plate 820. The windows or openings 822 may be defined within the plate 820 by stamping, through a photoetching technique or by cutting, as those of skill in this art will recognize.

FIG. 8C shows a perspective and a cross sectional view of still another exemplary configuration of the integrated cut and collect assembly of the present invention. As shown therein, the cutting portion of the integrated cut and collect assembly 108 may be an elliptical cylinder that defines an interior lumen 853. The cutting portion 852 may be energized with RF energy, as discussed above. A mandrel 854 may be disposed within the cutting portion 852. A slot 856 is defined only within the trailing edge 858, and not within the leading (cutting) edge 860 of the cutting portion 851 of the integrated cut and collect assembly 108. The flexible membrane 114 loops around the mandrel and emerges from the cutting portion 852 from the slot 856. The flexible membrane 114 may be bonded at 862 after looping around the mandrel 854. Alternatively, the mandrel 854 may be inserted in a lumen formed by the flexible membrane 114. As with the other embodiments discussed relative to FIGS. 6, 7 and 8, the flexible membrane may also be attached to the outer surface of the shaft 104 by means of a tab, such as shown at reference numeral 220 in FIG. 2C, so as to allow the bag-shaped flexible membrane 114 to selectively open an close upon being acted upon by actuator 112.

FIG. 8D shows yet another exemplary configuration of the integrated cut and collect assembly of the present invention, detailing the manner in which the collecting portion may be attached to the cutting portion of the integrated cut and collect assembly. As shown therein, the integrated cut and collect assembly 108 may be configured as a single ribbon 876 that defines a cutting portion 872 and a collecting portion 874. The single ribbon 876 may be split at least along the length of the trough 120 of the shaft 104. The distal ends of the cutting portion 872 and of the collecting portion 874 may be rejoined or may remain separate. The membrane 114 may define a lumen in which the free end of the collecting portion 874 may be introduced. Alternatively, the membrane 114 may be wrapped around the collecting portion 874 and secured thereto by means of an adhesive. The cutting portion 872 of the single ribbon 876 forms the leading edge of the integrated cut and collect assembly 108 as the device is rotated within the tissue and the specimen cut from the surrounding mass of tissue.

FIG. 8E shows another exemplary configuration of the integrated cut and collect assembly 108 of the present invention. The top figure of FIG. 8E shows the integrated cut and collect assembly 108 in the retracted position whereas the bottom figure shows the integrated cut and collect assembly 108 in the expanded position. As shown in the top figure, the membrane 114, when the integrated cut and collect assembly 108 is in the retracted position, is stretched across the trough 120. In this embodiment, the cutting portion of the integrated cut and collect assembly 108 may include a cutting ribbon 116 that emerges through the membrane 114 through a first slit therethrough and returns to the trough 120 through a second slit or opening defined therethrough. The cutting ribbon 116, therefore, is configured to be exposed to the tissue to be cut when the device is inserted within the patient and is located on a first external-facing surface of the membrane 114. The collecting portion of the integrated cut and collect assembly 108 may also include a collecting ribbon 118 that is located on a second surface of the membrane 114. The membrane may be attached to the shaft 104 such that when the integrated cut and collect assembly 108 is expanded in the radial direction relative to the shaft 104, the collecting ribbon 118 stretches the membrane 114 and causes the bag-shaped membrane 114 to define the mouth 222 (see FIG. 2C) of the collecting portion. After opening of the mouth or opening 222 by expansion of the integrated cut and collect assembly 108 and the stretching of the membrane 114 and after tissue has been collecting in the membrane 114, the integrated cut and collect assembly 108 may be retracted at least partially within the trough 120, causing the membrane 114 to return to the configuration shown in the top drawing of FIG. 8E. That is, the membrane 114 stretches back over the trough 120, thereby at least partially isolating the collected specimen from the surrounding tissue. In this embodiment, the collecting ribbon 118 may not be attached to the membrane 114. Indeed, the collecting ribbon 118 may only act upon the membrane 114 to stretch the membrane 114 open by pushing on it in the radial direction. When the specimen has been collected and the integrated cut and collect assembly integrated cutting and collecting assembly 108 retracted at least partially within the trough 120, the resilient nature of the membrane 114 causes the membrane to stretch back over the trough 120.

The foregoing has detailed a number of exemplary embodiments of the integrated cut and collect assembly 108. Those of skill in the art, however, may devise other alternative configurations and structures to integrate the cutting and collecting functions of reference numeral 108 into a single, mechanically coupled assembly that is actuable by a single actuator, such as shown at 112. All such alternative configurations, however, are deemed to fall within the purview of the present invention.

Figure 9:
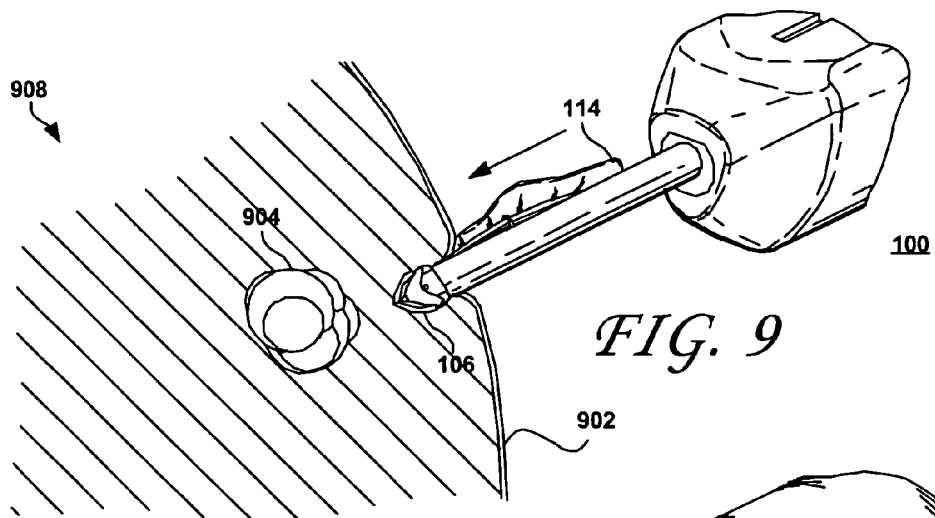
FIG. 9 illustrates aspects of the present method for cutting and collecting a tissue specimen from a mass of tissue, according to an embodiment of the present invention.
Figure 10:
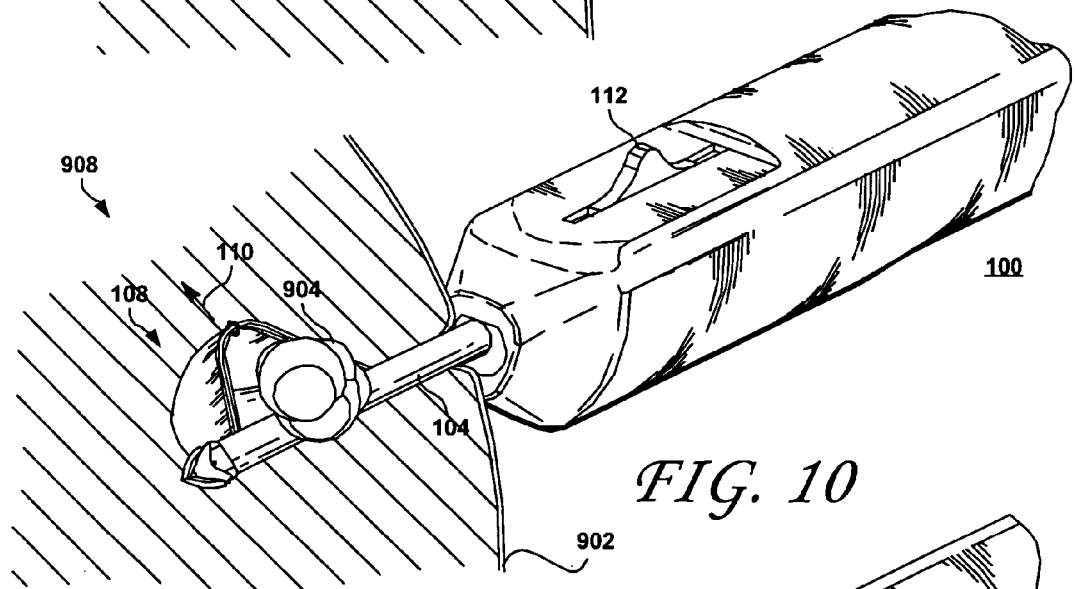
FIG. 10 illustrates further aspects of the present method for cutting and collecting a tissue specimen from a mass of tissue, according to an embodiment of the present invention.
Figure 11:
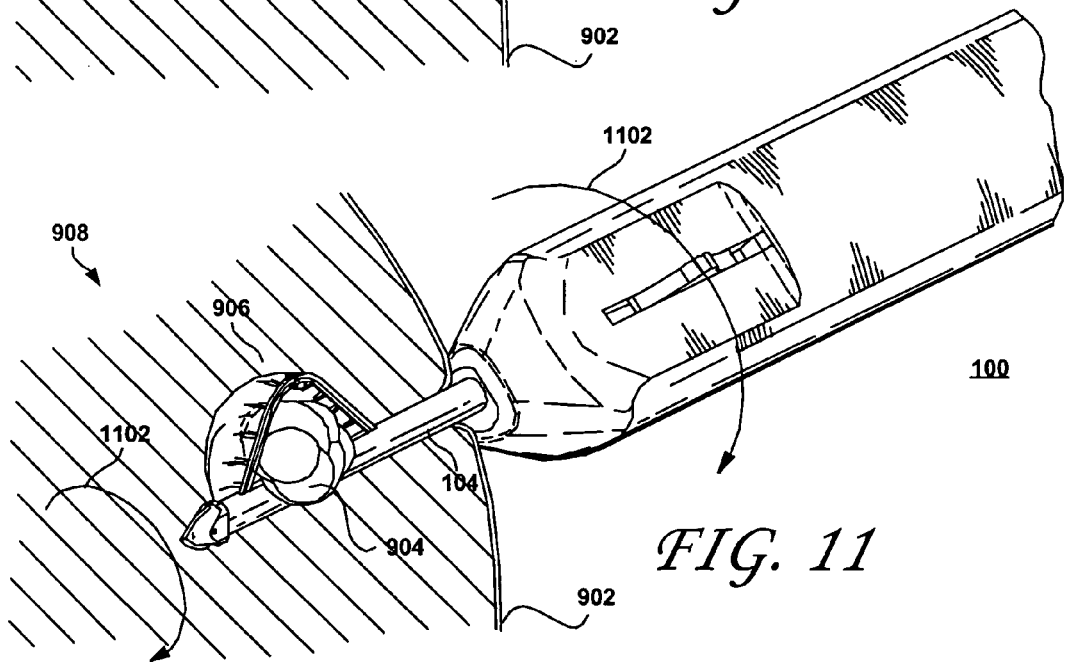
FIG. 11 illustrates still further aspects of the present method for cutting and collecting a tissue specimen from a mass of tissue, according to an embodiment of the present invention.
Figure 12:
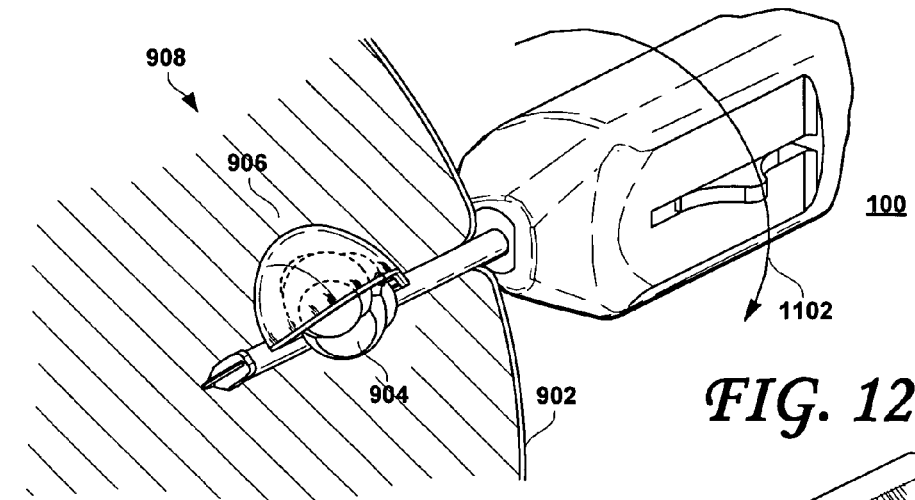
FIG. 12 illustrates further aspects of the present method for cutting and collecting a tissue specimen from a mass of tissue, according to an embodiment of the present invention.
Figure 13:
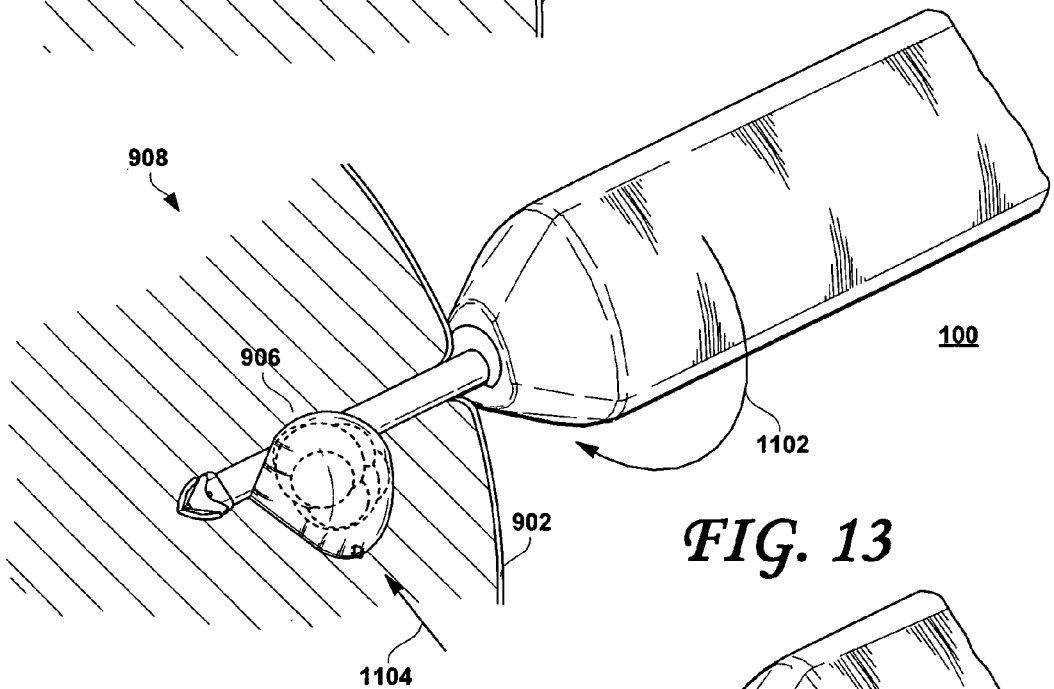
FIG. 13 illustrates further aspects of the present method for cutting and collecting a tissue specimen from a mass of tissue, according to an embodiment of the present invention.
Figure 14:
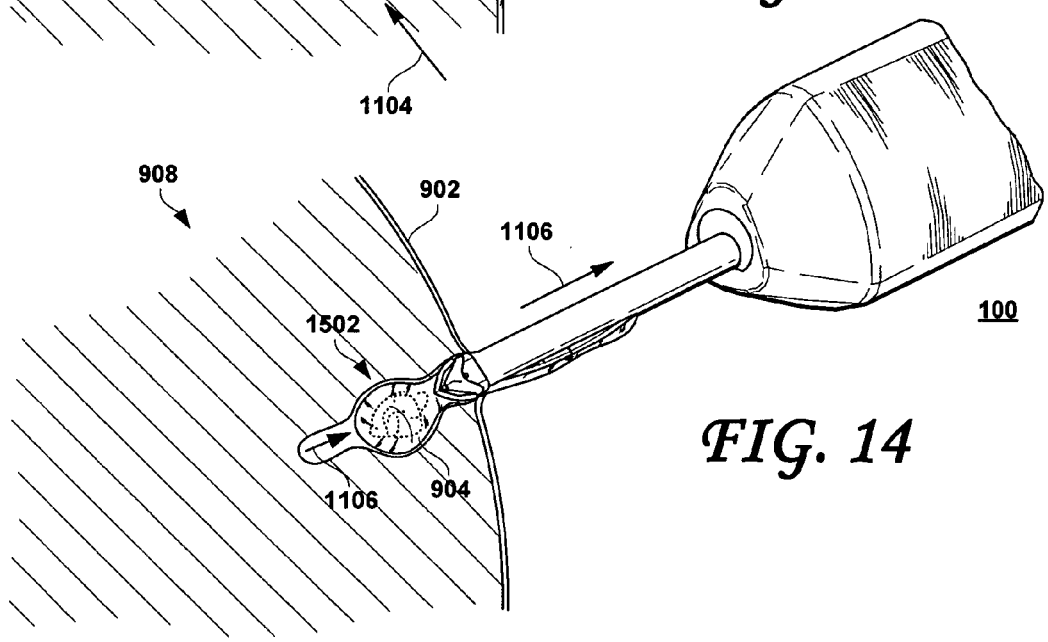
FIG. 14 illustrates further aspects of the present method for cutting and collecting a tissue specimen from a mass of tissue, according to an embodiment of the present invention in which the collected and isolated (encapsulated) tissue specimen trails the distal tip of the excisional device as it is retracted from the tissue.

FIGS. 9-16 show aspects of the present method for isolating a tissue specimen from surrounding tissue, according to embodiments of the present invention. As shown in FIG. 9, the excisional device 100 according to an embodiment of the present invention may be inserted through the skin 902 (or through the outermost tissue surface of the mass or organ from which the specimen is to be collected), either by making a prior incision therein or by allowing the distal tip 106 of the device 100 to make the initial cut. The distal tip 106 may be energized with RF energy during the insertion of the device 100 into the mass of tissue 908, but need not be. Satisfactory results are obtained by equipping the distal tip 106 with sharp blades and a conical shape, without the need for an RF energized tip. The integrated cut and collect assembly 108 should be initially in the retracted position, to enable it to readily penetrate the mass of tissue and advance to the target area (in this exemplary case, lesion 904) with the smallest possible profile. The shaft 104 may then be advanced (either through manual physician control or by means of a stereotactic setup) to a position wherein the integrated cut and collect assembly 108 is adjacent the target 904 and the target is approximately positioned in the middle of the integrated cut and collect assembly 108. As shown in FIG. 10, when the integrated cut and collect assembly 108 of the device 100 is positioned adjacent the target lesion 904, the integrated cut and collect assembly 108 may be expanded in the direction indicated by 110 by acting upon the actuator 112, after having fully energized the integrated cut and collect assembly 108 with RF energy, preferably while the integrated cut and collect assembly 108 is at least partially retracted within the trough 120. The integrated cut and collect assembly 108 may be expanded to up to its maximum expansion or to a selectable degree of expansion, advantageously under real time ultrasonic guidance and/or under another imaging modality. As shown at FIG. 11, the present excisional device 100 may then be rotated in the direction indicated by arrow 1102, while the integrated cut and collect assembly 108 remains energized with RF energy. In this manner, the leading edge of the RF-energized integrated cut and collect assembly 108 cuts through the tissue. Preferably the integrated cut and collect assembly 108 is expanded to a sufficient degree so as to cut a margin of healthy tissue around the target lesion 904, so as to decrease the probability of seeding abnormal cells (e.g., cancerous or pre-cancerous) into and around the excision site and the retraction path. As shown in FIG. 11, as the energized integrated cut and collect assembly 108 is rotated, it cuts around the lesion 904. As the trailing edge of the integrated cut and collect assembly 108 has deployed the collecting portion thereof, the cut lesion or specimen 904 is collected in the open bag formed by the trailing and close ended flexible membrane 114. As shown in FIGS. 12 and 13, the rotation 1102 of the device 100 may be continued as needed (preferably under ultrasonic guidance) until the specimen 904 has been at least partially severed from the surrounding tissue 906. At this point, the specimen 904 has been at least partially collected within the bag-shaped flexible membrane 114 of the collecting portion of the integrated cut and collect assembly 108. As shown at FIG. 14, to fully sever the specimen 904 from the surrounding tissue 906, the integrated cut and collect assembly 108, while still RF energized, may be retracted by acting proximally upon the actuator 112, thus causing the integrated cut and collect assembly 108 to move in the direction 1104 to capture and encapsulate the specimen 904 within the flexible membrane 114. As the bag-shaped flexible membrane is now closed, the cut and collected specimen is effectively isolated and encapsulated (or substantially isolated and encapsulated) from the surrounding tissue 906. Indeed, the cut and collected specimen 904 is now separated from the surrounding tissue by a layer of the flexible membrane 114. The RF to the integrated cut and collect assembly 108 may now be turned off.

As shown in FIG. 14, the cut, collected, encapsulated and isolated specimen 904 may then be recovered by retracting the device 100 from the mass of tissue 908 by moving the device 100 along the direction indicated at 1106. As shown in FIG. 14, the material of the flexible membrane 114 may be sufficiently elastics so as to allow the cut, collected and physically isolated specimen to stretch so as to at least partially trail the distal tip 106 as the device 100 is retracted along the insertion path through the mass of tissue 908, as shown at 1502 in FIG. 14. By configuring the integrated cut and collect assembly 108 So as to allow the specimen filled bag-shaped flexible membrane 114 to trail the distal tip 106, the initial incision into the skin and the diameter of the insertion and retraction path may be kept small, as neither the retraction path nor the incision need accommodate the full aggregate width of the shaft 104, the integrated cut and collect assembly 108 and the isolated specimen 904.

Figure 15:
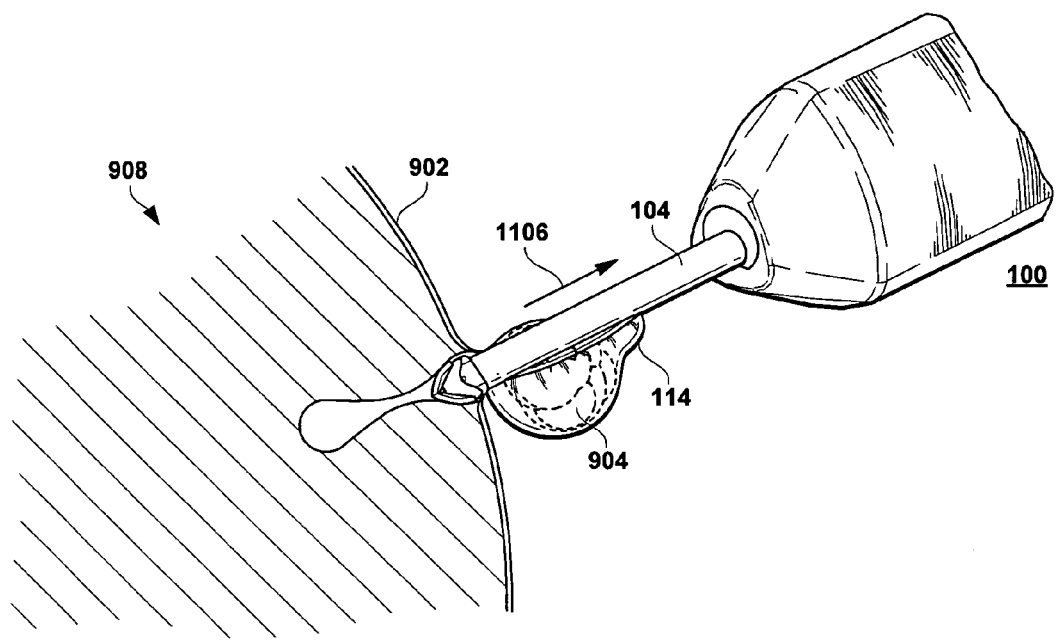
FIG. 15 illustrates further aspects of the present method for cutting and collecting a tissue specimen from a mass of tissue, according to another embodiment of the present invention in which the collected and isolated tissue specimen trails the distal end of the excisional device as it is retracted from the tissue.
Figure 16:
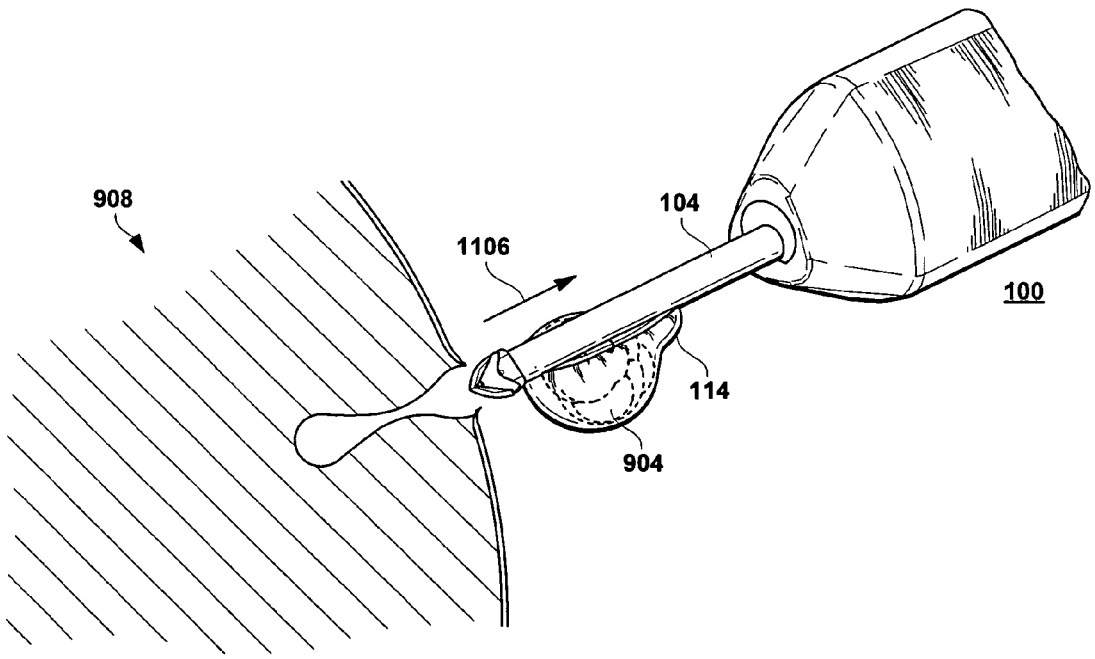
FIG. 16 illustrates still further aspects of the present method for cutting and collecting a tissue specimen from a mass of tissue, in which the excisional device containing the tissue specimen has been fully removed from the tissue mass from which the specimen was cut, collected and isolated.

As shown in FIG. 15, the specimen-filled flexible membrane of the collecting portion of the integrated cut and collect assembly 108 may be configured so that it does not substantially trail the distal tip, or only does so partially during retraction of the device 100 from the mass of tissue from which the specimen was cut. The material of the flexible membrane 114 (as detailed below) and the configuration thereof may be chosen so as to achieve the desired behavior during the collecting, isolating and retracting phases of the present method. FIG. 16 shows a fully retracted device 100, containing a collected and isolated specimen 904 in which the tissue architecture has been maintained substantially intact. After full retraction of the device 100 from the mass of tissue, the incision within the skin 904 may be treated and closed according to standard surgical practices. During the excisional method detailed relative to FIGS. 9-16, the second lumen 206 (shown in FIG. 2A) within the shaft 104 may be used, for example, to evacuate smoke and/or bodily fluids (e.g., blood) from the excision site within the mass of tissue 908. Alternatively the second lumen 206 defined within the shaft 104 may be used to deliver a pharmaceutical agent to the excisional site, such as, for example, an anesthetic, an analgesic and/or some other agent. The inflatable balloon 208 shown in FIG. 2A may be may be inflated with, for example, a gas (air or carbon dioxide, for example) or a fluid (such as saline, for example). The balloon 208 may assist in stabilizing the present excisional device within the tissue mass after insertion therein and/or to provide some degree of hemostasis during the excisional procedure.

The flexible membrane 114 is preferably non-conductive and stable at high temperatures. For example, the material used in the flexible membrane should be RF resistant (i.e., have the ability to withstand the temperatures generated by the RF-energized cutting portion of the integrated cut and collect assembly integrated cutting and collecting assembly 108). The flexible membrane 11, therefore, should be stable (i.e., acceptably maintains its structural integrity and does not unacceptably melt, deform, burn or loose cohesion, tensile or shear strength) at temperatures at which the energized cutting portion operates. According to one embodiment of the present invention, the flexible membrane includes a non-main chain carbon based polymeric material, such as a silicone elastomer (such as polydimethylsiloxane, for example) or a silicone-containing elastomer. For example, the flexible membrane 114 of the collecting portion of the integrated cut and collect assembly 108 may include one or more of the following materials: an organic, inorganic or organic-inorganic polymer such as a silicone elastomer or a silicone-containing elastomer, a teraphthalate, a tetrafluoroethylene, a polytetrafluoroethylene, a polyimid, a polyester, a polyolephin, Kevlar® and/or M5®, for example. The flexible membrane 114 may have a laminar structure that includes one or more reinforcing layers. Such reinforcing layers may include, for example, any of the above-listed materials and/or polyester, polyurethane or polyimid, for example. For example, the flexible membrane 114 may include NuSil 10-6640, a material manufactured by NuSil Technology of Carpinteria, Calif. The thickness of the flexible membrane may be freely chosen according to the desired characteristics of the collecting portion of the integrated cut and collect assembly 108. For example, the flexible membrane 114 may be between about 0.0005 and about 0.1 inches, for example. For example, the flexible membrane 114 may be chosen to have a thickness between about 0.0007 and 0.005 inches. For example, the flexible membrane 114 may be selected to have a thickness of between 0.001 and 0.015 inches.

When an adhesive is used to secure the flexible membrane to other structures of the device or the integrated cut and collect assembly 108, a strong, biologically inert and safe adhesive may be used. Advantageously, a silicone containing or based adhesive or a cyanoacrylate containing or based adhesive may be used with good results.

Figure 17:
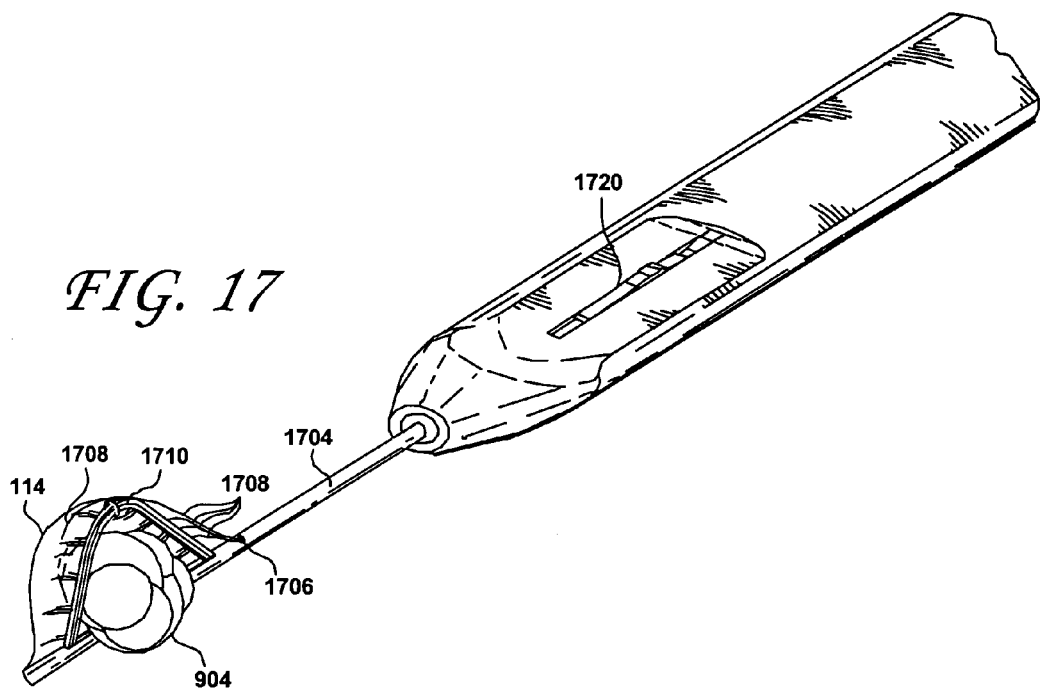
FIG. 17 shows aspects of another embodiment of the present invention.
Figure 18:
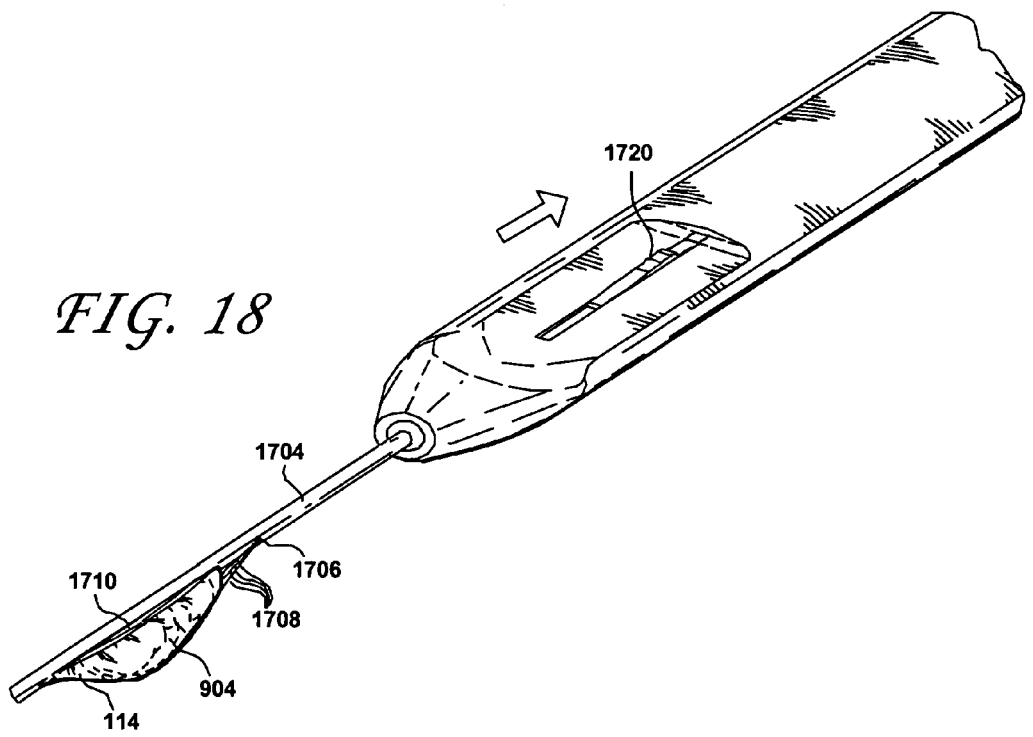
FIG. 18 shows the embodiment of FIG. 18 in a state in which the collected specimen is drawn toward the shaft prior to retraction of the device.

FIG. 17 shows a device for collecting a specimen from a mass of tissue, according to another embodiment of the present invention. As shown therein, the device includes a shaft 1704 that defines a proximal end (adjacent the handle) and a distal end (at the free end of the shaft 1704). A specimen collection assembly 1710 is disposed near the distal end of the shaft 1704. The specimen collection assembly 1710 may include a flexible membrane 114 configured to collect the specimen, as detailed above. The specimen collection assembly 1710 may also include a tissue cutting assembly, as detailed above. According to the embodiment of the present invention illustrated in FIGS. 17 and 18, the device may also include a specimen management assembly that is coupled to the specimen collection assembly 1710. The specimen collection assembly 1710 is configured to assume a variable expanded configuration as shown in FIG. 17 and a retracted configuration shown in FIG. 18. In use, the specimen management assembly is configured to draw the specimen collected in the flexible membrane 114 toward the shaft 1704. By drawing the specimen 904 collected in the flexible membrane 114 toward the shaft 1704 when the specimen collection assembly 1710 is in its retracted position (FIG. 18), the specimen 904 may be compressed and/or may be elongated within the flexible membrane and along the shaft 1704. This compression and/or elongation may streamline the profile of the specimen collection assembly 1710 and enclosed specimen 904. In turn, a more streamlined profile may ease the retraction of the device from mass of tissue in which it was inserted and from the patient without necessitating a large incision or enlarging the incision made to insert the device. In the embodiments shown in FIGS. 17 and 18, the specimen management assembly is coupled to the flexible membrane 114 of the specimen collection assembly 1710. Any structure that draws the specimen 904 toward the shaft 1704, however, may be used and falls within the scope of the present invention. For example, and as shown in FIGS. 17 and 18, the specimen management assembly may configured to selectively pull on the flexible membrane 114 in at least one direction that is parallel to the shaft 1704 (i.e., toward the proximal end of the shaft 1704 and/or toward the distal end of the shaft 1704). Indeed, by pulling on the flexible membrane 114 when the specimen collection assembly 1710 is in its retracted state (FIG. 18), the specimen 904 may be somewhat compressed by the flexible membrane 114 in a direction that is generally perpendicular to the longitudinal axis of the shaft 1704 and/or somewhat elongated in a direction that is parallel to the longitudinal axis of the shaft 1704. For example, the specimen management assembly may, for example, pull the flexible membrane 114 toward the distal end of the shaft 1704. Alternatively, the specimen management assembly may, for example, pull the flexible membrane 114 toward the proximal end of the shaft 1704, as shown in FIGS. 17 and 18.

As shown therein, one or more wires 1708 may be attached to the flexible membrane 114. Within the context of the present invention, the term "wire" is to be interpreted broadly and is intended to encompass structures such as cables, strings, filaments, threads, cords, ribbons as well as structures such as fabrics, meshworks, lattices and the like. The wire(s) 1708 may be formed of any strong and surgically suitable material that may attach to the flexible membrane 114, such as, for example, Kevlar® or M5® material. The distal ends of the wires 1708 may be attached to various points on the flexible membrane 114. The proximal end of the wires 1708 may be attached to an actuator, such as shown at 1720. In this manner, when the actuator 1720 is pushed distally, the specimen collection assembly may assume its expanded configuration shown in FIG. 17 and the wires 1708 may be loose. Conversely, when the actuator 1720 is pulled proximally (as shown in FIG. 18), the wires 1708 may be tightened and pull on the flexible membrane 114. Alternatively, the proximal end o the wires 1708 may be coupled to a wire actuator (not shown) that may be separate and distinct from the actuator 1720.

As noted above, during the collection of the specimen 904 (FIG. 17), the wire or wire(s) 1708 are preferably loose and preferably do not pull on the flexible membrane 114. After the specimen 904 has been collected (FIG. 18) and isolated within the flexible membrane 114 from the surrounding tissue by retracting the specimen collection assembly, the wires 1708 may pull on the flexible membrane 114 to reduce the radial height of the collected specimen 904 over the shaft 1704, as shown in FIG. 18. In FIG. 18, the wires 1708 are taut and pull on the flexible membrane 114, thereby somewhat compressing and/or elongating the specimen 904. As shown, the wires 1708 may run within a lumen defined within the shaft 1704 and may emerge to attach to the flexible membrane through a bore 1706 defined between the interior lumen of the shaft 1704 and the external surface thereof. The wires 1708 may instead be attached to the distal portion of the flexible membrane 114, travel to the distal end of the shaft 1704 and back to the actuator 1720. For example, the wires 1708 may slide over a pin disposed within the distal end of the shaft 1704. Alternatively still, either the distal or proximal portions of the flexible membrane 114 may be attached to the shaft 1704 while the wires 1708 may be attached to the other one of the distal and proximal ends not attached to the wires 1708. In this manner, one side or portion of the flexible membrane 114 may be anchored to the shaft 1704 and the other side or portion pulled by the wires 1708. For example, as shown in FIGS. 17 and 18, the distal portion of the flexible membrane 114 may be attached to the shaft 1704 while the proximal portion of the flexible membrane 114 may be selectively and variably pulled by the wires 1708 to draw the specimen 904 toward the shaft 1704, to thereby reshape the flexible membrane 904 and the collected specimen 904. This effectively reduces the resistance of the entire device within the tissue and makes it easier to maneuver the device within the tissue. More particularly, the reshaped flexible membrane 114 and collected specimen 904 eases the retraction of the device back through the dissection (entry) path and through a smaller incision that would otherwise be possible had the flexible membrane 114 and the specimen collected therein maintained their original profile.

Figure 19:
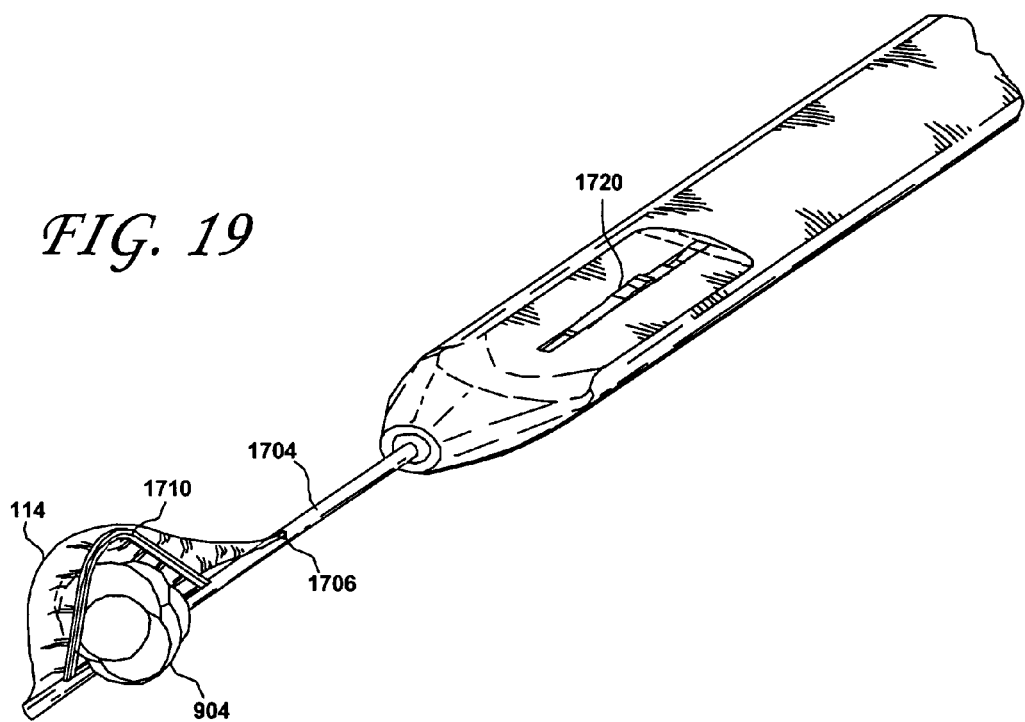
FIG. 19 shows aspects of yet another embodiment of the present invention.
Figure 20:
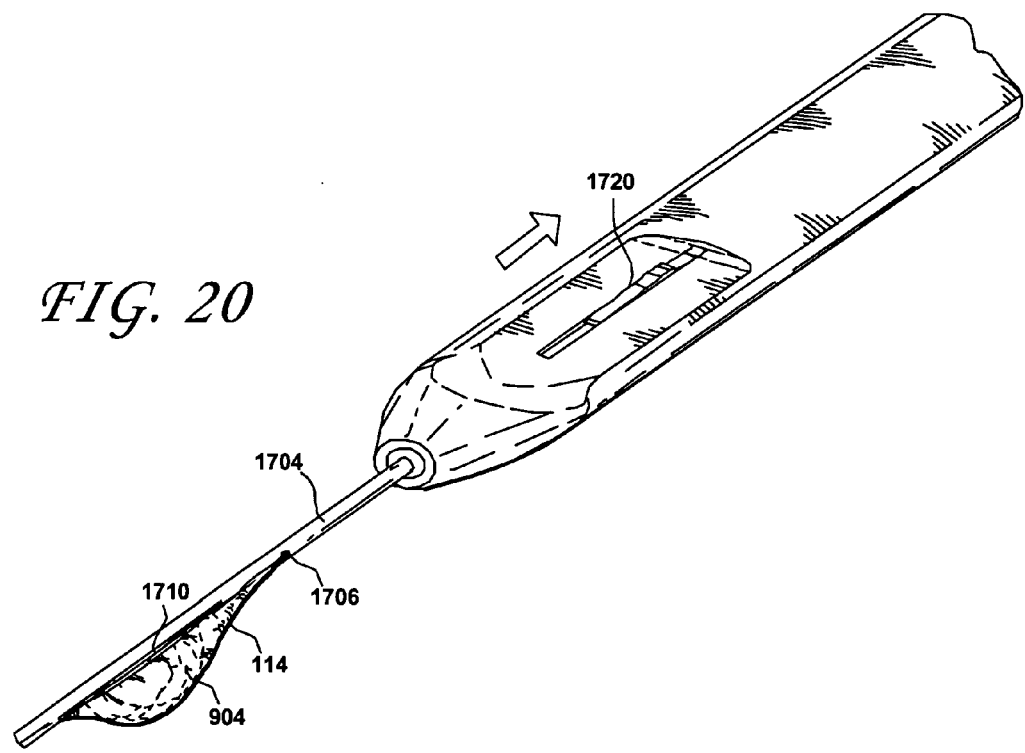
FIG. 20 shows the embodiment of FIG. 19 in a state in which the collected specimen is drawn toward the shaft prior to retraction of the device.

FIGS. 19 and 20 show aspects of another embodiment of the present invention. As shown therein, instead of wires, ribbons or cords 1708, the flexible membrane 114 itself may be pulled in the proximal and/or distal directions to draw the collected specimen 904 toward the shaft 1704. One end of the flexible membrane 114 may be secured to the shaft 1704. The flexible membrane may include an extension that runs through a bore 1706 to a lumen within the shaft 1704, to the actuator 1720 or another independent actuator (not shown). Alternatively still, the flexible membrane extension may be attached to one or more wires 1708 that run to an actuator, as described above. This embodiment is functionally similar to the embodiment of FIGS. 17 and 18, as the collected specimen 904 is drawn toward the shaft 1704 by similarly directed forces.

The wires, ribbons or cords 1708 advantageously also operate to re-shape the tract from the incision to the cavity created by the collected specimen. Indeed, the wires, ribbons or cords 1708 cause the collection assembly 1710 containing the specimen 904 to present a more tapered profile as the device is retracted from the patient. The shape of the flexible membrane bag 114 in FIGS. 19 and 20 also presents a tapered profile that eases the retraction of the device from the tract after the specimen 904 has been cut, collected and shaped.

Figure 21:
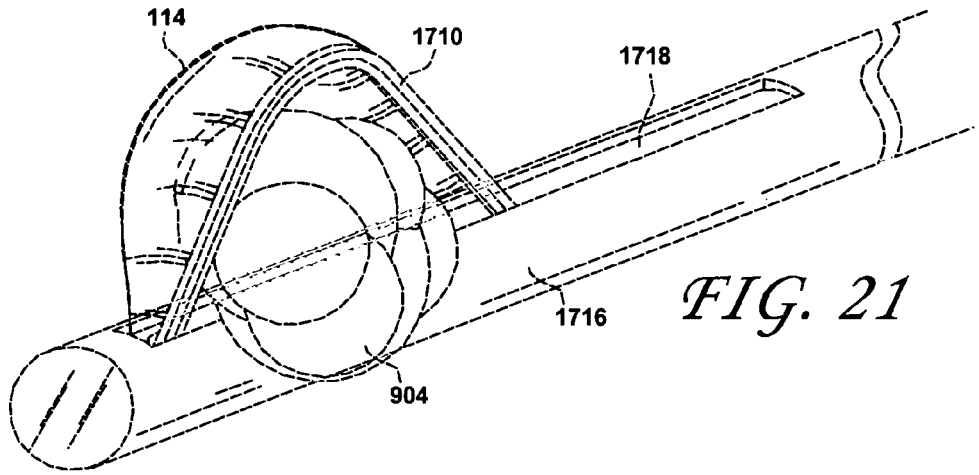
FIG. 21 shows a portion of another embodiment of an excisional device according to the present invention.
Figure 22:
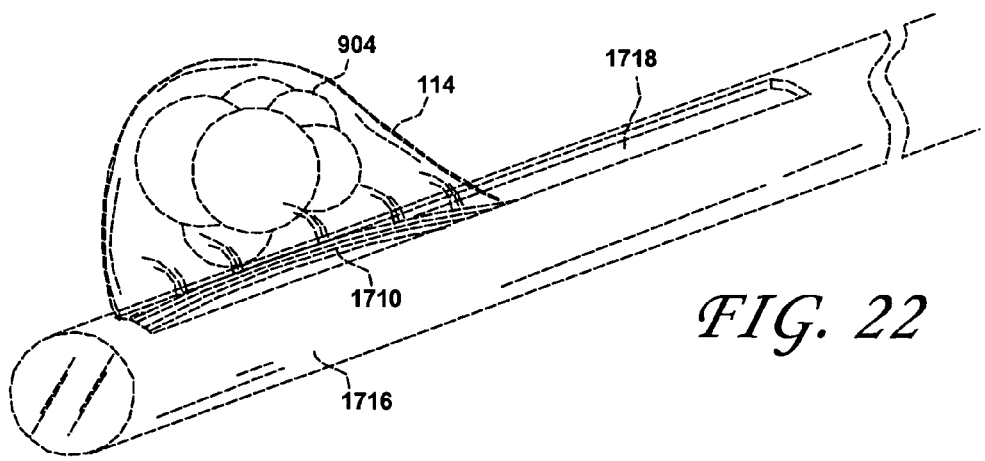
FIG. 22 shows further aspects of the embodiment of FIG. 21.
Figure 23:
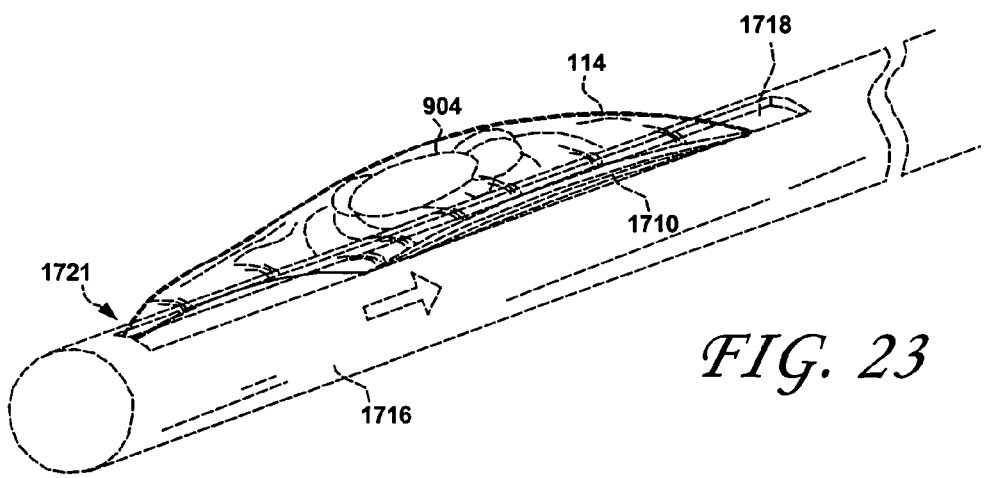
FIG. 23 shows still further aspects of the embodiment of FIG. 21.

FIGS. 21-23 illustrate aspects of another embodiment of the present invention. More particularly, FIGS. 21-23 show the distal portion of the shaft 1716 of a tissue collection device according to another embodiment of the present invention. The proximal portion thereof is not shown in FIGS. 21-23, for clarity of illustration. As shown, the shaft 1716 may define a channel 1718 along at least a portion of its length. The specimen collection assembly 1710 is free to selectably slide within the channel 1718 from the proximal end thereof the distal end thereof. When the device is initially inserted in the patient, the specimen collection assembly 1710 and attached flexible membrane 114 may be proximally retracted, so as to provide the least amount of resistance with the surrounding tissue during the insertion. Thereafter, when the distal portion of the shaft 1716 has been maneuvered adjacent the target lesion or other tissue to be collected, biopsied or otherwise excised, the specimen collection assembly 1710 and attached flexible membrane may be distally slid and more or less centered on the target lesion, under ultrasonic guidance, for example. As shown in FIG. 21, the specimen collection assembly 1710 may then be caused to assume its expanded configuration shown.

In the case wherein the specimen collection assembly 1710 includes a specimen cutting assembly (such as an RF cutter, for example), the shaft 1716 may be rotated and the target lesion severed from the surrounding tissue to create the specimen as detailed above. In so doing, the flexible membrane 114 may be deployed and encapsulate the created specimen; In the case wherein the tissue collection specimen does not include a specimen cutting assembly and the specimen has already been created (i.e., the target lesion severed from surrounding tissue) but has not but not yet collected, the tissue specimen collection assembly 1710 may be expanded, rotated and retracted to the configuration shown in FIG. 22 to collect and isolate the specimen 904 from the surrounding tissue within the flexible membrane 114.

The devices according to the embodiments of the present invention described herein, however, may cut and collect tissue specimens 904 that are larger than the initial incision made in the patient to introduce the device in the patient. To avoid having to enlarge the incision and/or the retraction path of the device and to prevent such incision from tearing or stretching during withdrawal of the collected and isolated specimen 904, it may necessary to streamline or otherwise alter the shape of the specimen collected within the flexible membrane 114. This may reduce its profile and facilitate withdrawal of the device and collected specimen from the patient. To do so, the specimen collection assembly 1710 containing the collected specimen 904 may be slid within the channel 1718 in the proximal direction, as shown in FIG. 23. As a portion (the distal portion, for example) of the flexible membrane may be attached (either directly or through other structures) to the distal end of the shaft as shown at 1721, the flexible membrane 114 and the collected and isolated specimen 904 will be drawn against the shaft 1716, thereby forming a slimmer profile and easing the removal of the device from the patient. Indeed, as the specimen collection assembly 1710 and the attached flexible membrane 114 is retracted in the proximal direction while a portion of the flexible membrane remains attached to the distal end of the shaft 1716, the flexible membrane 114 will tighten around the collected specimen 904, thereby drawing it closer to the shaft 1716, somewhat compressing and/or elongating the specimen 904 in the process. Instead of or in addition to the channel 1718, the specimen collection assembly 1710 may slide in the proximal and distal directions on a rail running along the shaft 1716. The embodiment of FIGS. 21-23 may be used in conjunction with some or all of the structures shown and described relative to FIGS. 17-20. Other means of drawing a collected specimen toward the shaft and/or reshaping the collected specimen to ease retraction of the collection device may occur to those of skill in this art and all such variations are deemed to fall within the scope of the present invention.

Figure 24:
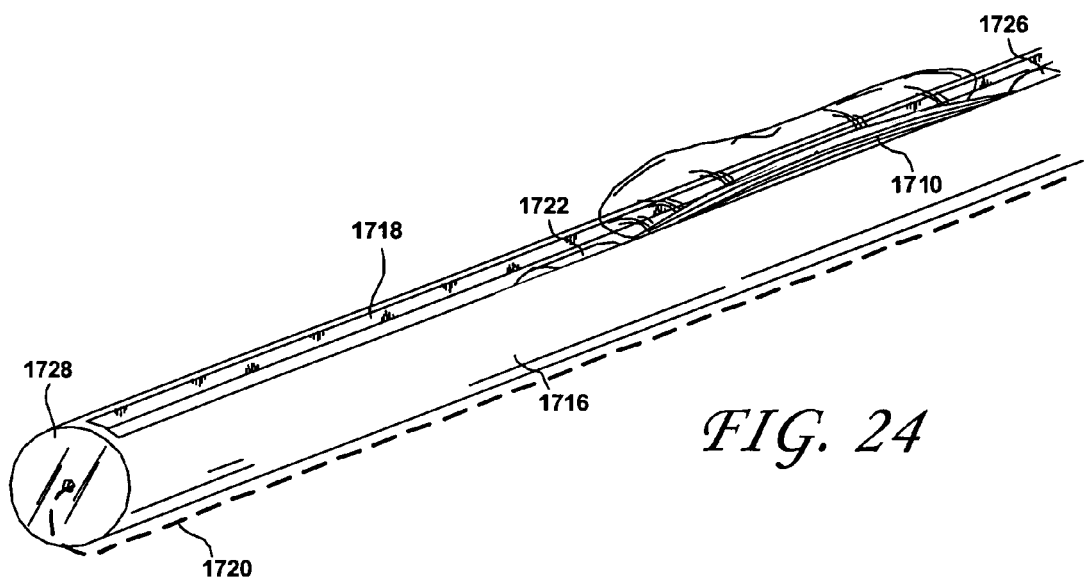
FIG. 24 is a perspective view of a distal portion of the shaft of an excisional device in a first configuration, according to a sill further embodiment of the present invention.
Figure 25:
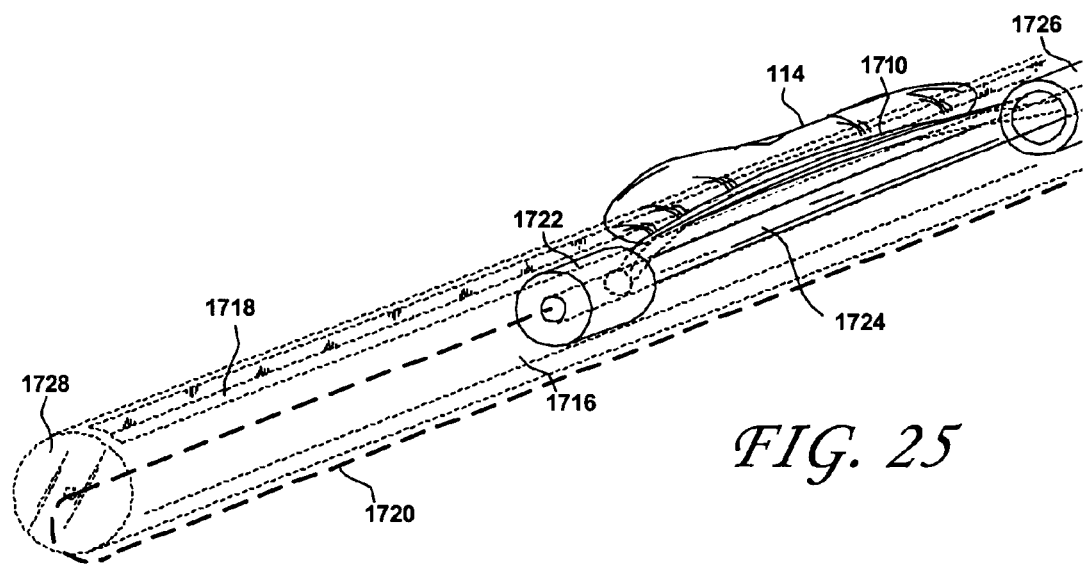
FIG. 25 shows the embodiment of FIG. 24, with the shaft represented in phantom lines to reveal further structural aspects thereof.
Figure 26:
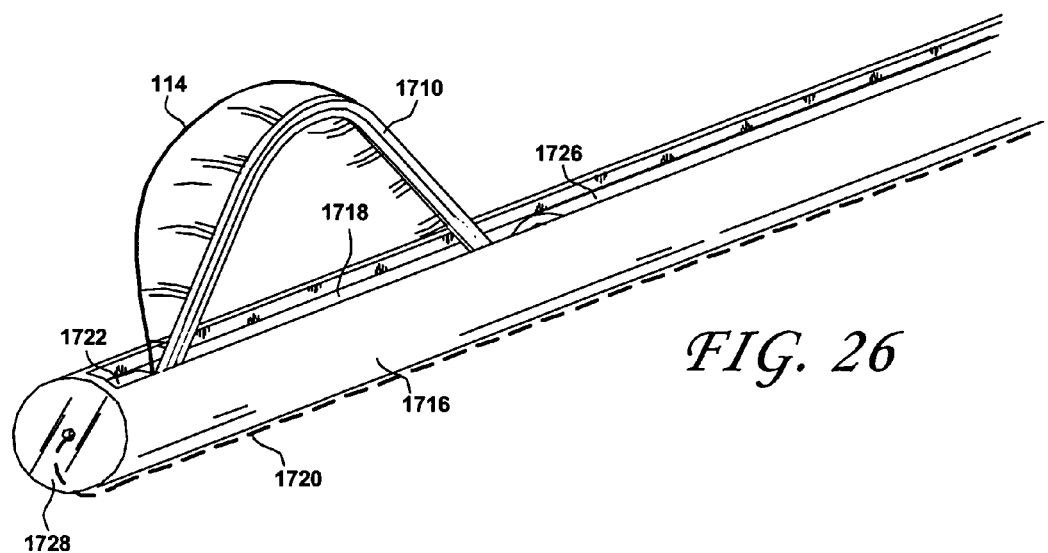
FIG. 26 shows a perspective view of the embodiment of FIG. 24 in a second configuration.
Figure 27:
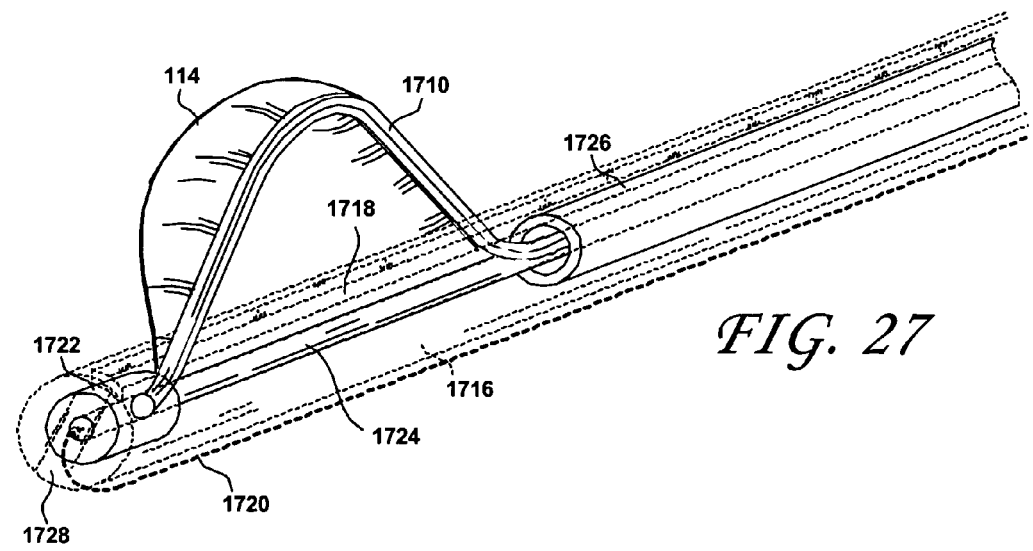
FIG. 27 shows the embodiment of FIG. 26, with the shaft represented in phantom lines to reveal further structural aspects thereof.

FIG. 24 is a perspective view of a distal portion of the shaft of an excisional device in a first configuration, according to a sill further embodiment of the present invention. FIG. 25 shows the embodiment of FIG. 24, with the shaft represented in phantom (dashed) lines to reveal further structural aspects of this embodiment. Similarly, FIG. 26 is a perspective view of a distal portion of the shaft of the excisional device of FIGS. 24 and 25 in a second configuration. FIG. 27 shows the embodiment of FIGS. 24-26, with the shaft represented in phantom lines to reveal exemplary internal structure. Considering now FIGS. 24-27 collectively, the shaft 1716 may define a channel or other opening 1718 and the specimen collection assembly 1710 may be configured to selectively slide between the proximal end and distal ends of the shaft 1716. The channel 1718 may be defined from the distal end of the shaft 1716 to the proximal end thereof, or only a portion of the distance therebetween. In FIGS. 24 and 25, the specimen collection assembly 1710 is in its first configuration, closer to the proximal end of the shaft 1716 than to the distal end thereof. Conversely, FIGS. 26 and 27 show the present excisional device in a second configuration in which the specimen collection assembly 1710 is closer to the distal end of the shaft 1710 than to the proximal end thereof. To ease insertion of the shaft 1716 into the patient, the shaft may be inserted into the patient in the first configuration in which the specimen collection assembly 1710 is in the first configuration shown in FIGS. 24 and 25. That is, prior to inserting the shaft 1716 into the patient, the physician may slide the specimen collection assembly 1710 at least partially along the channel 1718 in the proximal direction, so as to present smoother profile as the device is inserted into the tissue.

The distal tip of the shaft 1716 of the embodiments shown in FIGS. 17-29 may have any suitable configuration that is effective to penetrate and maneuver the shaft 1716 within tissue. The distal tip may, for example, have a sharp edge, may have an RF-powered element or may have any other surgically suitable structure. FIGS. 17-27 generically show the distal tip as a blunt surface, for ease of illustration only.

When the excisional device according to the embodiment of FIGS. 24-27 has been positioned adjacent or near the target lesion or specimen, the specimen collection assembly 1710 may be slid in the distal direction so as to cause the excisional device to assume the configuration shown in FIGS. 26-27. Moreover, after the specimen has been collected within the flexible membrane 114, the specimen collection assembly 1710 may again be slid from the distal end of the shaft 1716 toward the proximal end thereof, if desired (before, during or after the physician retracts the device along the dissection or retraction path). In addition, the collected specimen may be drawn toward the shaft 1716, as described herein relative to FIGS. 17-23 or by other means. While the specimen 904 is being drawn toward the shaft 1716 and while the specimen collection assembly 1710 is being slid toward the proximal direction, the specimen 904 remains encapsulated by the flexible membrane 114 and isolated from the surrounding tissue, to minimize or eliminate the chance of seeding potentially abnormal cells (e.g., cancerous cells) in the retraction path of the excisional device or in any of the surrounding tissue.

FIGS. 25 and 27 show the shaft 1716 in phantom lines to reveal exemplary internal structure of the excisional device according to this embodiment of the present invention. The specimen collection assembly 1710 may be configured to selectively slide between a proximal position (FIGS. 24-25) and a distal position (FIGS. 26-27) by various means. As shown in FIGS. 25 and 27, the distal end of the specimen collection assembly 1710 may be coupled to a slider 1722. The slider 1722 may be configured to slide within the shaft 1716. The travel of the slider 1722 in the distal direction may be limited by abutting against the distal end 1728 of the shaft 1716. To slide within the shaft 1710, the slider 1722 may be attached to a flexible wire 1720. The wire 1720 may be routed to the distal end of 1728 of the shaft 1716 via a through bore defined in the distal end 1728 and thereafter back to a suitable actuator on the proximal end 102 (the handle) of the present excisional device. In that case, pulling on the wire 1720 causes the slider 1722 to slide within the shaft 1716 in the distal direction. The wire 1720 may be partially external to the shaft 116 as shown in FIGS. 24-27 or may be entirely accommodated within the shaft 1716. To retract the slider 1722 and the specimen collection assembly 1710 in the proximal direction, the physician may cause the specimen collection assembly 1710 to assume its retracted position (FIGS. 24-25) in the manner described above and may thereafter further pull on the specimen collection assembly 1710 in the proximal direction, thereby causing the cutting and/or collecting ribbon(s) thereof to pull the attached slider 1722 in the proximal direction.

Alternatively (or in addition to the wire 1720), the slider 1722 may also be coupled to a rigid member 1724 within the shaft 1716. In that case, sliding the slider 1722 within the shaft 1726 may be accomplished by pushing or pulling on the rigid member 1724. Sliding the slider 1722 in the distal direction, therefore, may rely on the column strength of the rigid member 1724. The shaft 1716 may also accommodate an internal cannula 1726. The cannula 1726 may be movable within the shaft 1716. During use of the excisional device, the cannula 1726 may cooperate with the slider 177 to position the specimen collection assembly 1710 adjacent the specimen to be cut and/or collected. The proximal portions of the cutting and/or collection ribbons of the specimen collection assembly 1710 as well as the proximal portion of the rigid member 1724 may be disposed within an internal lumen of the cannula 1726, as shown in FIGS. 25 and 27. The distance along the longitudinal axis of the shaft 1716 between the slider 1722 and the cannula 1726 defines the distance over which the specimen collection assembly 1710 may bow (as shown in FIGS. 26 and 27). Toward that end, the cannula 1726 may itself slide within the shaft 1716, as may be seen by comparing the relative positions of the cannula 1726 in FIGS. 25 and 27. In use, the combination of the slider 1722, the rigid member 1724, the cannula 1726 and the specimen collection assembly 1710 may be slid all the way in the proximal or distal directions or may be locked in an intermediate position therebetween and the specimen collection assembly 1710 expanded in such a locked position. Suitable actuators may be disposed on the proximal end 102 (the handle) of the present excisional device to effectuate such sliding and/or locking functions. Of course, other mechanisms and assemblies for sliding the specimen collection assembly 1710 within a channel 1718 may be devised, as those of skill in this art may recognize. As noted above, the embodiments shown and described relative to FIGS. 17-23 may be implemented in combination with the embodiment shown in FIGS. 24-27 to draw the collected specimen toward the shaft 1716 to ease retraction of the device from the patient after the specimen 904 has been collected. To enable the flexible membrane 114 of the specimen collection assembly 1710 to slide between proximal and distal positions within the shaft 1716, the flexible membrane 114 may advantageously be attached to the rigid member 1724 as well as to the collection ribbon of the specimen collection assembly 1710. In this manner, the flexible membrane 114 may form a bag shape whose opening is defined by the rigid member 1724 and the collection ribbon of the specimen collection assembly 1710. When the specimen collection assembly 1710 is in its retracted or collapsed configuration (FIGS. 24-25), the opening of the bag-shaped flexible membrane 114 is closed, thereby substantially sealing the collected specimen 904 therein. Indeed, when the specimen collection assembly 1710 is in its retracted configuration, the collection ribbon to which the flexible membrane 114 is attached is in a position that is adjacent the rigid member 1724 to which the flexible membrane 114 is also attached, thereby effectively closing the bag-shaped flexible membrane 114 and isolating the collected specimen within the flexible membrane.

According to another embodiment, the distal end 1728 of the shaft 1716 may be open and the shaft 1716 may be removable (i.e., detachable) from the handle of the device. In that case, after the tissue or lesion has been cut and collected, the shaft 1716 may be detached from the handle of the device and slid in the proximal direction, leaving the collection assembly 1710 in place within the patient. The collection assembly may then be separately removed. Detaching the shaft 1716 from the device prior to retraction of the collection assembly 1710 may ease the retraction of a large specimen through the incision by allowing the collection assembly to occupy the space previously occupied by the shaft 1716. Alternately, the channel 1718 and the collection assembly may be configured so as to enable the collection assembly to be slid proximally out through the incision and removed from the shaft 1716. The channel 1716 may thereafter be used as a guide to introduce other items into the lesion or specimen cavity, such as a balloon to stop bleeding, a marker or an endoscope, for example.

Figure 28:
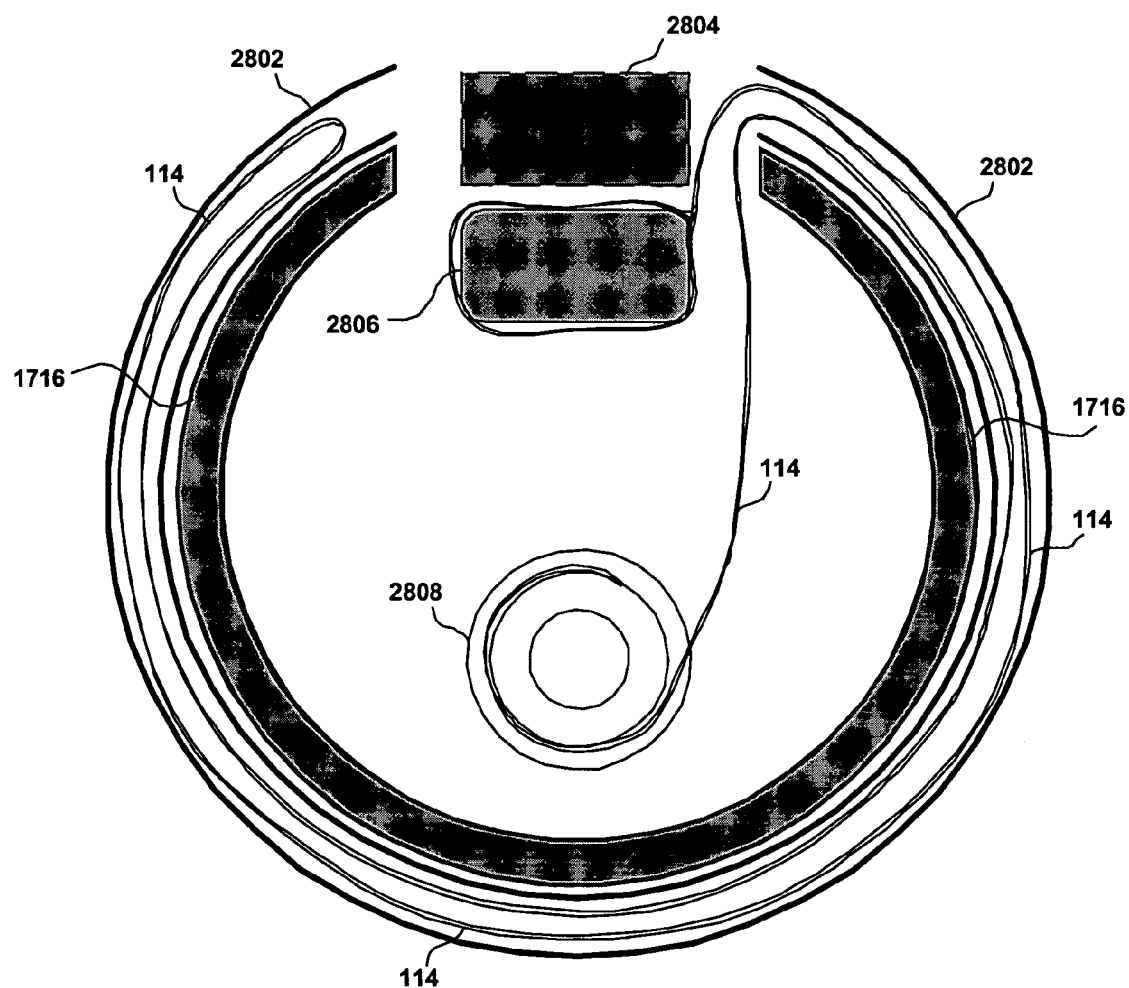
FIG. 28 is a cross-sectional view of another embodiment of the present invention in which at least a portion of the shaft of the present excisional device is covered by a sleeve, to ease the insertion and/or retraction of the present excisional device into and from a mass of tissue.
Figure 29:
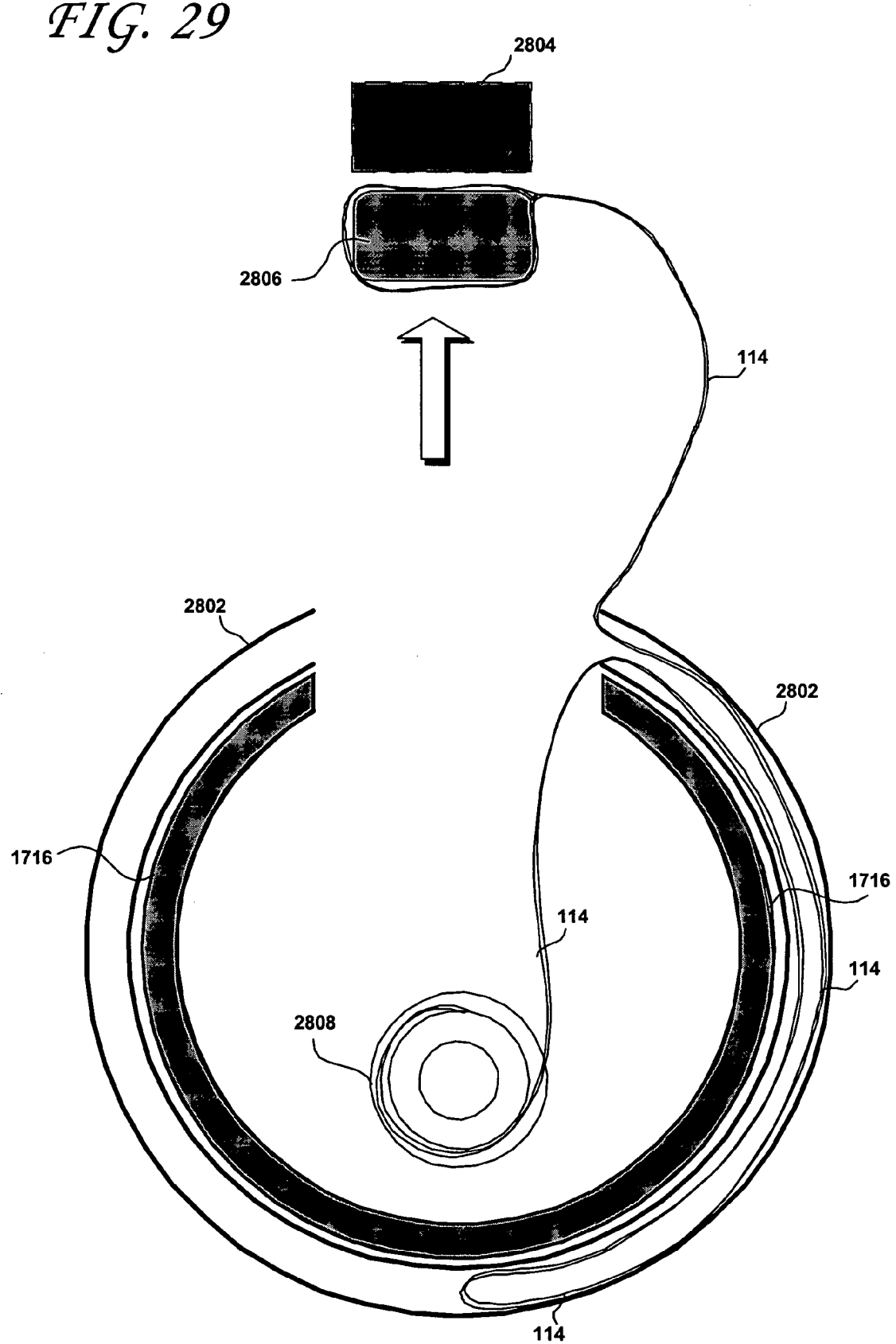
FIG. 29 is a cross-sectional view of the embodiment of FIG. 28, with the tissue collection assembly of the present excisional device in an expanded configuration.

FIG. 28 is a cross-sectional view of the shaft of another embodiment of the present invention. According to this embodiment, at least a portion of the shaft 1716 is covered by a sleeve, to ease the insertion and/or retraction of the present excisional device into and from a mass of tissue. FIG. 29 is a cross-sectional view of the embodiment of FIG. 28, with the specimen collection assembly of the present excisional device in an expanded configuration. In this embodiment, the shaft is designated by reference numeral 1716, the flexible membrane by reference numeral 114 and the collection ribbon of the specimen collection assembly by reference numeral 2806. The specimen collection assembly may also include a cutting ribbon, shown in phantom lines at reference numeral 2804. The collection ribbon and the cutting ribbon may be attached to one another or may be independently actuable. According to this embodiment, a sleeve 2802 covers at least a portion of the circumference and length of the shaft, such as shaft 1716 in FIGS. 24-27. Such a sleeve 2802 may ease at least the insertion of the shaft 1716 into the patient's tissue. According to one embodiment, the sleeve 2802 may be retracted prior to the specimen collection assembly being expanded and the device rotated to collect a previously cut specimen or to cut and collect a specimen from a surrounding mass of tissue. According to another embodiment and as shown in FIGS. 28 and 29, a window or cutout may be defined within the sleeve in such a manner as to align with the channel 1718 and/or otherwise allow the expansion and retraction of the specimen collection assembly in the radial direction. The window or cutout defined within the sleeve 2802 may also allow the specimen collection assembly to slide in the proximal and distal directions, in the manner described relative to FIGS. 24-27, for example. According to an embodiment of the present invention, to further reduce the drag of the flexible membrane against the tissue during insertion of the excisional device into the patient's tissue and the manipulation thereof to bring the shaft 1716 in adjacency with the target lesion or specimen to be collected or cut and collected, the flexible membrane 114 may be initially at least partially stowed between an internal surface of the sleeve 2802 and an external surface of the shaft 1716, as shown in FIGS. 28 and 29. As shown therein, the flexible membrane 114 may be wrapped around the outer surface of the shaft, with the sleeve 2802 fitting over the flexible membrane 114. FIG. 28 shows the flexible membrane attached at one end to a membrane support 2808 and thereafter running between the sleeve and the shaft 1716 at least partially around the circumferences thereof. As shown the flexible membrane 114 may then double back upon itself, and may thereafter attach to, for example, the collection ribbon 2806 of the specimen collection assembly. As shown this end of the flexible membrane 114 may wrap around the tissue collection ribbon 2806. The specimen collection assembly may also include a cutting ribbon (shown in phantom line) 2804, which may be independent from the collection ribbon 2806 or coupled thereto, as described previously herein.

When the specimen collection assembly is expanded (e.g., bowed in the radial direction), the collection ribbon 2806 bows radially away from the shaft 1716 and may assume the configuration shown in FIG. 29. As shown therein, the collection ribbon 2806 pulls on the flexible membrane initially stowed between the shaft 1716 and the sleeve 2802. As the collection ribbon 2806 rises, the flexible membrane 114 is at least partially pulled out of its stowed configuration and follows the collection ribbon 2806. As the present excisional device is then rotated and the specimen collected (or cut and collected), more or all of the flexible membrane 114 may be pulled from between the shaft 1716 and the sleeve 2802. Advantageously, the flexible membrane 114 does not generate increased friction against the tissue during insertion of the device into the patient's tissue and/or during the fine displacements of the shaft 1716 that may be required to precisely locate the distal portion thereof adjacent to target tissue to be collected and/or excised and collected. Also, because the flexible membrane 114 is pulled from between the shaft 1716 and the sleeve 2804 when the collection assembly is deployed, it is unlikely to interfere with the RF cutting of the cutting ribbon 2804. Indeed, in this configuration, the flexible membrane is unlikely to fold against the leading (e.g., cutting) edge of the cutting ribbon 2804. Moreover, the rotation of the device (for example, counterclockwise in FIGS. 28 and 29, may insure that the flexible membrane always trails behind the cutting ribbon 2804, thereby insuring that both the cutting and collecting operations occur without interference from the flexible membrane as it is deployed and pulled from between the sleeve 2804 and the shaft 1716.

While the foregoing detailed description has described preferred embodiments of the present invention, it is to be understood that the above description is illustrative only and not limiting of the disclosed invention. For example, those of skill in this art may envisage other means of reducing drag and/or re-shaping the collected specimen prior to retraction of the present and like devices from the patient's tissue. Indeed, those of skill in this art will recognize other alternative embodiments and all such embodiments are deemed to fall within the scope of the present invention. Thus, the present invention should be limited only by the claims as set forth below.

What is claimed is:

1. A method of collecting a specimen from a mass of tissue, comprising the steps of:
   providing a tissue collection device comprising a shaft and a specimen collection assembly, the shaft defining a proximal and a distal end and including a rail between the proximal and distal ends, the specimen collection assembly being configured to slide between the proximal and distal ends and to selectively expand away from the shaft and to contract toward the shaft, the specimen collection assembly including a flexible membrane configured to collect the specimen;
   inserting the tissue collection device within the mass of tissue;
   expanding the specimen collection assembly and collecting the specimen within the flexible membrane;
   retracting the specimen collection assembly with the specimen collected within the flexible membrane;
   sliding the retracted specimen collection assembly on the rail toward the proximal end of the shaft with the specimen collected within the flexible membrane.

2. The method of claim 1, wherein the tissue collection device in the providing step includes a tissue cutting portion to cut the specimen from the mass of tissue.

3. The method of claim 2, wherein the collecting step collects the specimen cut from the cutting portion.

4. The method of claim 1, further including a step of sliding the specimen collection assembly toward the distal end of the shaft before the inserting step.

5. The method of claim 1 wherein, in the inserting step, the tissue collection device is in a configuration in which flue specimen collection assembly is slid toward the distal end of the shaft.

6. The method of claim 1, further comprising a step of sliding the specimen collection assembly toward the distal end of the shaft before the expanding and collecting steps.

7. The method of claim 1, wherein the tissue collection device in the providing step is configured such that a portion of the flexible membrane is attached to the distal end of the shaft, and wherein the sliding step draws the specimen collected within the flexible membrane toward the shaft.

8. The method of claim 1, flutter comprising the step of retracting the tissue collection device from the mass of tissue with the specimen collection assembly near the proximal end of the shaft and the specimen collected within the flexible membrane.

9. The method of claim 1, wherein the retracting step isolates the specimen collected within the flexible membrane from the mass of tissue.

10. The method of claim 1 wherein, in the providing step, the shaft defines a channel between the proximal and distal ends of the shaft and wherein the sliding step slides the retracted specimen collection assembly within the channel.

11. A method of collecting a specimen from a mass of tissue, comprising the steps of:
    providing a tissue collection device comprising a shaft defining a proximal and a distal end, a sleeve disposed over at least a portion of the shaft and a specimen collection assembly configured to selectively expand away from the shaft and to retract toward the shaft and including a flexible membrane configured to collect the specimen, at least a portion of the flexible membrane being disposed between the shaft and the sleeve, the sleeve defining a cutout aligned so as to allow the specimen collection assembly to expand and retract therethrough;
    inserting the tissue collection device within the mass of tissue with the sleeve covering at least a portion of the sleeve and at least a portion of the specimen collection assembly;
    expanding the specimen collection assembly through the sleeve and collecting the specimen within the flexible membrane, the expanding specimen collection assembly pulling the flexible membrane out from between the shaft and the sleeve, and
    retracting the specimen collection assembly through the sleeve with the specimen collected within the flexible membrane.

12. The method of claim 11, further comprising a step of proximally retracting the sleeve to expose the specimen collection assembly to the mass of tissue prior to the inserting step.

13. The method of claim 11, wherein the providing step is carried out with at least the portion of the sleeve wrapped around an outer surface of the shaft.

* * * * *

UNITED STATES PATENT AND TRADEMARK OFFICE
CERTIFICATE OF CORRECTION

PATENT NO. : 7,615,013 B2 Page 1 of 1
APPLICATION NO. : 11/441627
DATED : November 10, 2009
INVENTOR(S) : Mark J. Clifford et al.

It is certified that error appears in the above-identified patent and that said Letters Patent is hereby corrected as shown below:

Col. 26 line 13 replace

"tissue collection device is in a configuration in which flue" with

"tissue collection device is in a configuration in which the".

Signed and Sealed this

Sixteenth Day of February, 2010

David J. Kappos
*Director of the United States Patent and Trademark Office*